United States Patent [19]

Bailey

[11] 4,206,215

[45] Jun. 3, 1980

[54] ANTIMICROBIAL BIS-[4-(SUBSTITUTED-AMINO)-1-PYRIDINIUM]ALKANES

[75] Inventor: Denis M. Bailey, East Greenbush, N.Y.

[73] Assignee: Sterling Drug Inc., New York, N.Y.

[21] Appl. No.: 876,031

[22] Filed: Feb. 8, 1978

Related U.S. Application Data

[63] Continuation-in-part of Ser. No. 721,315, Sep. 7, 1976, abandoned, which is a continuation-in-part of Ser. No. 661,101, Feb. 25, 1976, abandoned.

[30] Foreign Application Priority Data

Feb. 11, 1977 [GB] United Kingdom ............... 5784/77

[51] Int. Cl.$^2$ .................. C07D 213/02; A61R 31/44
[52] U.S. Cl. ............................. 424/263; 546/261; 546/264; 252/106
[58] Field of Search ............... 260/296 D; 252/106; 424/263; 546/261, 264

[56] References Cited

U.S. PATENT DOCUMENTS

| | | | |
|---|---|---|---|
| 3,055,902 | 9/1962 | Walker | 260/296 D |
| 3,786,058 | 1/1974 | Edwards | 260/294.8 R |

OTHER PUBLICATIONS

Walker et al., J. Org. Chem., vol. 26, pp. 2740–2747, (1961).
Austin, J. Pharm. Pharmacol., vol. 11, pp. 80–93, (1959).

*Primary Examiner*—John D. Randolph
*Attorney, Agent, or Firm*—Paul E. Dupont; B. Woodrow Wyatt

[57] ABSTRACT

Bis-[4-(R-amino)-1-pyridinium]alkanes are prepared by reacting a 4-(R-amino)pyridine with an appropriate disubstituted alkane. The compounds are useful as antimicrobial agents. Certain species are also useful as dental plaque-preventive agents.

45 Claims, No Drawings

ANTIMICROBIAL BIS-[4-(SUBSTITUTED-AMINO)-1-PYRIDINIUM]ALKANES

CROSS-REFERENCE TO RELATED APPLICATION

This application is a continuation-in-part of prior copending application Ser. No. 721,315, filed Sept. 7, 1976, now abandoned, in turn a continuation-in-part of application Ser. No. 661,101, filed Feb. 25, 1976 and now abandoned.

BACKGROUND OF THE INVENTION

1. Field of the Invention

The present invention relates to compositions of matter classified in the art of chemistry as bis-[4-(R-amino)-1-pyridinium]alkanes, to a process for the preparation thereof, to compositions containing these compounds and to methods of using the same for controlling microorganisms and for preventing the formation of dental plaque.

2. Prior Art

Walker U.S. Pat. No. 3,055,902, issued Sept. 25, 1962 discloses a group of bis-(4-amino-1-pyridinium)alkanes. No utility is disclosed for these compounds other than as intermediates in the preparation of the corresponding bis-(4-amino-1-piperidino)alkanes which are stated to have bacteriostatic and bactericidal effects.

G. N. Walker et al., J. Org. Chem. 26, 2740-7 (1961) disclose essentially the subject matter disclosed in the above-noted Walker U.S. patent.

W. C. Austin et al., J. Pharm. Pharmacol. 11, 80-93 (1959) disclose 1,10-bis-(4-amino-1-pyridinium)decane diiodide and 1,10-bis(4-acetamido-1-pyridinium)decane diiodide. It is stated that certain species among the large, diverse group of quaternary ammonium compounds disclosed possess amebicidal, antibacterial, antifilarial and trypanocidal activity, but no biological data are given for either of the above-named compounds.

Edwards U.S. Pat. No. 3,786,058, issued Jan. 15, 1974 discloses a group of bis(pyridinium quaternary salts) believed to be structurally more remote from the claimed compounds than the above-noted Walker and Austin et al. compounds and having the formula

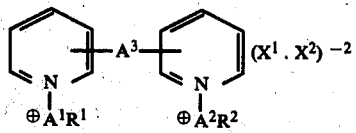

wherein inter alia:

$R_1$ and $R_2$ are alkyl of 6 to 14 carbon atoms;
$A_1$ and $A_2$ are a direct linkage;
$A_3$ is $-NH(CH_2)_mNH-$, m being 0 to 12; and
$X^1.X^2$ represents two monoanions or a dianion. It is stated that the compounds possess antibacterial properties and that some are useful in dental hygiene for inhibiting the formation of dental plaque. In the above compounds the pyridinium groups are linked through an alkylene diamine chain bonded to the carbon atoms of the pyridine rings and thus constitute a class of compounds which are separate and distinct from the instantly claimed bis-(pyridinium)alkanes in which the pyridinium groups are linked through an alkylene group bonded to the nitrogen atoms of the pyridine rings.

SUMMARY OF THE INVENTION

In a composition aspect, this invention relates to a group of bis-[4-(R-amino)-1-pyridinium]alkanes which are useful as antimicrobial agents. Certain of the compounds are also useful as dental plaque-preventive agents.

In a further composition aspect the present invention provides an antimicrobial composition suitable for topical administration comprising an effective amount of a bis-[4-(R-amino)-1-pyridinium]alkane and a compatible, pharmaceutically acceptable carrier.

In another composition aspect, this invention relates to a skin-cleansing composition comprising an antimicrobially effective amount of a bis-[4-(R-amino)-1-pyridinium]-alkane, a compatible, pharmaceutically acceptable surfactant and a compatible, pharmaceutically acceptable carrier.

In yet another composition aspect, this invention provides an oral hygiene composition for the prevention of dental plaque comprising an effective amount of a dental plaque-preventive bis-[4-(R-amino)-1-pyridinium]alkane and a compatible, pharmaceutically acceptable carrier.

In another composition aspect, the present invention provides an antimicrobial composition suitable for application to inanimate surfaces comprising an antimicrobially effective amount of a bis-[4-(R-amino)-1-pyridinium]alkane in admixture with a compatible vehicle.

In a method aspect, the present invention provides a method for controlling microorganisms which comprises contacting said microorganisms with an antimicrobially effective amount of a bis-[4-(R-amino)-1-pyridinium]alkane.

In a further method aspect, this invention is concerned with a method for treating teeth to prevent the formation of dental plaque thereon which comprises contacting the teeth with an effective amount of a dental plaque-preventive bis-[4-(R-amino)-1-pyridinium]alkane.

DETAILED DESCRIPTION INCLUSIVE OF THE PREFERRED EMBODIMENTS

The invention sought to be patented resides in one of its composition aspects in the bis-[4-(R-amino)-1-pyridinium]-alkanes having Formula I hereinbelow:

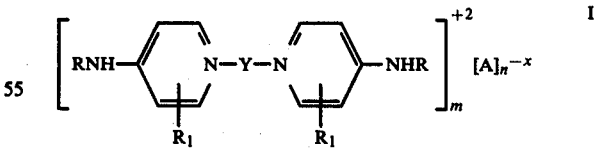

wherein:
Y is an alkkylene group containing from 4 to 18 carbon atoms and separating the two 4-(R-NH)-1-pyridinyl groups by from 4 to 18 carbon atoms;
R is an alkyl group containing from 6 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl;
$R_1$ is hydrogen or lower alkyl;

A is an anion;
m is 1 or 3;
n is 1 or 2;
x is 1, 2 or 3; and
wherein (m)(2)=(n)(x).

These compounds are useful as antibacterial and antifungal agents and are virucidally active against Herpes viruses.

Included in the above group are the compounds having Formula I wherein Y, A, $R_1$, m, n and x have the abovegiven meaning and wherein:

(a) R is an alkyl group containing from 6 to 18 carbon atoms;

(b) R is a cycloalkyl group containing from 5 to 7 carbon atoms;

(c) R is phenyl substituted by methylenedioxy or one or two substituents selected from the group consisting of halogen, lower-alkyl, lower-alkoxy, nitro, cyano and trifluoromethyl;

(d) R is benzyl.

Certain of the compounds of Formula I are also useful as dental plaque-preventive agents, for example:

1,6-Bis-[4-(octylamino)-1-pyridinium]hexane dibromide and the corresponding dichloride, 1,6-Bis-[4-(nonylamino)-1-pyridinium]hexane dibromide and the corresponding dichloride, 1,6-Bis-[4-(decylamino)-1-pyridinium]hexane dibromide, 1,6-Bis-[4-(dodecylamino)-1-pyridinium]hexane dibromide, 1,7-Bis-[4-(heptylamino)-1-pyridinium]heptane dibromide, 1,7-Bis-[4-(octylamino)-1-pyridinium]heptane dibromide, 1,7-Bis-[4-(nonylamino)-1-pyridinium]heptane dibromide, 1,7-Bis-[4-(decylamino)-1-pyridinium]heptane dibromide, 1,7-Bis-[4-(dodecylamino)-1-pyridinium]heptane dibromide, 1,8-Bis-[4-(heptylamino)-1-pyridinium]octane dibromide and the corresponding dichloride, 1,8-Bis-[4-(octylamino)-1-pyridinium]octane dichloride, 1,8-Bis-[4-(nonylamino)-1-pyridinium]octane dibromide, 1,8-Bis-[4-(decylamino)-1-pyridinium]octane dibromide, 1,8-Bis-[4-(dodecylamino)-1-pyridinium]octane dibromide, 1,8-Bis-[4-(2-ethylhexylamino)-1-pyridinium]-octane dibromide, 1,9-Bis-[4-(heptylamino)-1-pyridinium]nonane dichloride, 1,9-Bis-[4-(nonylamino)-1-pyridinium]nonane dibromide, 1,9-Bis-[4-(decylamino)-1-pyridinium]nonane dibromide, 1,9-Bis-[4-dodecylamino)-1-pyridinium]nonane dibromide, 1,10-Bis-[4-(heptylamino)-1-pyridinium]decane dibromide and the corresponding dichloride, 1,10-Bis-[4-(nonylamino)-1-pyridinium]decane dibromide, 1,10-Bis-[4-(decylamino)-1-pyridinium]decane dibromide, 1,10-Bis-[4-(dodecylamino)-1-pyridinium]decane dibromide, 1,10-Bis-[4-(2-ethylhexylamino)-1-pyridinium]-decane dichloride, 1,12-Bis-[4-(hexylamino)-1-pyridinium]dodecane dibromide and the corresponding dichloride, 1,12-Bis-[4-(heptylamino)-1-pyridinium]dodecane dibromide, 1,12-Bis-[4-(octylamino)-1-pyridinium]dodecane dibromide, 1,12-Bis-[4-(nonylamino)-1-pyridinium]dodecane dibromide, 1,12-Bis-[4-(decylamino)-1-pyridinium]dodecane dibromide, 1,12-Bis-[4-(dodecylamino)-1-pyridinium]dodecane dibromide, 1,12-Bis-[4-(2-ethylhexylamino)-1-pyridinium]-dodecane dibromide and the corresponding dichloride, 1,14-Bis-[4-(hexylamino)-1-pyridinium]tetradecane dibromide and the corresponding dichloride, 1,14-Bis-[4-(heptylamino)-1-pyridinium]tetradecane dibromide and the corresponding dichloride, 1,14-Bis-[4-(octylamino)-1-pyridinium]tetradecane dibromide, 1,10-Bis-[4-(octylamino)-1-pyridinium]decane bis(1-oxo-2-pyridinethiolate), and, as particularly preferred species, 1,9-Bis-[4-(heptylamino)-1-pyridinium]nonane dibromide, 1,10-Bis-[4-(2-ethylhexylamino)-1-pyridinium]-decane dibromide, 1,10-Bis-[4-(octylamino)-1-pyridinium]decane dichloride and the corresponding dibromide, 1,9-Bis-[4-(octylamino)-1-pyridinium]nonane dibromide, 1,2-Bis-[4-(heptylamino)-1-pyridinium]dodecane dichloride, and 1,8-Bis-[4-(octylamino)-1-pyridinium]octane dibromide.

In a further composition aspect the invention sought to be patented resides in an antimicrobial composition suitable for topical administration which comprises an effective amount of a compound having the Formula I hereinabove and a compatible, pharmaceutically acceptable carrier.

In another composition aspect, the invention sought to be patented resides in a skin-cleansing composition comprising an antimicrobially effective amount of a compound having the Formula I hereinabove, a compatible, pharmaceutically acceptable surfactant and a compatible, pharmaceutically acceptable carrier.

In another composition aspect the invention sought to be patented resides in an oral hygiene composition for the prevention of dental plaque comprising an effective amount of a compound selected from the group consisting of 1,9-bis-[4-(heptylamino)-1-pyridinium]nonane dibromide, 1,10-bis-[4-(2-ethylhexylamino)-1-pyridinium]decane dibromide, 1,10-bis-[4-(octylamino)-1-pyridinium]decane dichloride, 1,9-bis-[4-(octylamino)-1-pyridinium]nonane dibromide, 1,12-bis-[4-(heptylamino)-1-pyridinium]dodecane dichloride, 1,8-bis-[4-(octylamino)-1-pyridinium]octane dibromide and 1,10-bis-[4-(octylamino)-1-pyridinium]decane dibromide and a compatible, pharmaceutically acceptable carrier.

In yet another composition aspect the invention sought to be patented resides in an antimicrobial composition suitable for application to inanimate surfaces comprising an effective amount of a compound having the Formula I hereinabove in admixture with a compatible vehicle.

In one of its method aspects the invention sought to be patented resides in the method for controlling microorganisms which comprises contacting said microorganisms with an antimicrobially effective amount of a compound having Formula I hereinabove wherein Y, $R_1$, A, m, n and x have the above given meanings, and wherein:

R is hydrogen, an alkyl group containing from 1 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl.

A preferred embodiment of the above-described method resides in the use therein as antimicrobial agent, a compound having Formula I wherein R is an alkyl group containing from 1 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl.

Also included within the ambit of the above method is the use of compounds wherein R is hydrogen. Several of these compounds are known in the prior art e.g. the Walker and Austin et al. references cited hereinabove. However, these references disclose no utility for these compounds except as intermediates. Accordingly, the discovery of antimicrobial activity therefor, albeit of substantially lower potency and narrower spectrum relative to the novel compounds, is considered within the scope of the present invention.

In another of its method aspects the invention sought to be patented resides in the method of treating teeth for preventing the formation of dental plaque thereon which comprises contacting the teeth with an effective amount of a compound selected from the group consisting of 1,9-bis-[4-heptylamino)-1-pyridinium]nonane dibromide, 1,10-bis-[4-(2-ethylhexylamino)-1-pyridinium]decane dibromide, 1,10-bis-[4-(octylamino)-1-pyridinium]decane dichloride, 1,9-bis[4-(octylamino)-1-pyridinium]nonane dibromide, 1,12-bis-[4-(heptylamino)-1-pyridinium]dodecane dichloride, 1,8-bis[4-(octylamino)-1-pyridinium]octane dibromide and 1,10-bis-[4-(octylamino)-1-pyridinium]decane dibromide.

Although the compounds of the present invention are conveniently represented by Formula I hereinabove, it will of course, be appreciated that electron-delocalized or resonance forms of Formula I (i.e. differing only in the position of electrons) such as Formulas Ia and Ib hereinbelow are equivalent representations of the instant compounds. The actual structure of the compounds in a resonance hybrid of Formulas I, Ia and Ib.

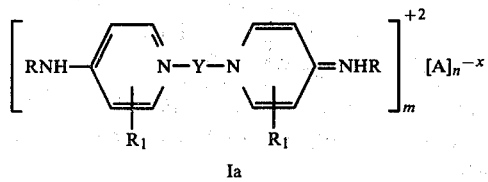

Ia

-continued

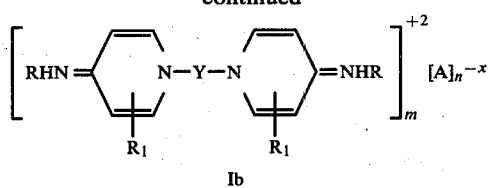

Ib

In the formulas herein the alkylene group Y is a bivalent saturated aliphatic hydrocarbon radical containing from 4 to 18, preferably from 8 to 12, carbon atoms arranged in a straight or in a branched chain and separating the two 4-(R-NH)-1-pyridinyl groups by from 4 to 18, preferably from 8 to 12, carbon atoms, for example:

1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,13-tridecylene, 1,14-tetradecylene, 1,15-pentadecylene, 1,16-hexadecylene, 1,17-heptadecylene, 1,18-octadecylene, 1-methyl-1,4-butylene, 3-methyl-1,5-pentylene, 2-ethyl-1,4-butylene, 3-methyl-1,6-hexylene, 2,4-dimethyl-1,5-pentylene, 1-methyl-1,7-heptylene, 3-ethyl-1,6-hexylene, 3-propyl-1,5-pentylene, 4,4-dimethyl-1,7-heptylene, 2,6-dimethyl-1,7-heptylene, 2,4,4-trimethyl-1,6-hexylene, 2,7-dimethyl-1,8octylene, 1-methyl-1,10-decylene, 5-ethyl-1,9-nonylene, 3,3,6,6-tetramethyl-1,8-octylene, 3,8-dimethyl-1,10-decylene, 3-methyl-1,11-undecylene, 6-methyl-1,12-dodecylene, 2-methyl-1,13-tridecylene, 4,9-dimethyl-1,12-dodecylene, 4-methyl-1,14-tetradecylene, 2,13-dimethyl-1,14-tetradecylene, 1,4-dipropyl-1,4-butylene, 3-(3-pentyl)-1,5-pentylene, 2-(4,8-dimethylnonyl)-1,4-butylene, 1-heptyl-1,5-pentylene, and the like.

It will be appreciated that when Y contains 4 carbon atoms the latter must, of course, be arranged in a straight chain and similarly when Y contains 18 carbon atoms and separates the two 4-(R-NH)-1-pyridinyl groups by 18 carbon atoms said carbon atoms must also be arranged in a straight chain. In all other instances Y can be either straight or branched.

In the formulas herein when R is a straight or branched-chain alkyl group containing from 6 to 18, there are included, for example:

n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, 1-methylpentyl, 2,2-dimethylbutyl, 2-methylhexyl, 1,4-dimethylpentyl, 2-ethylpentyl, 3-ethylpentyl, 2-methylheptyl, 1-ethylhexyl, 2-ethylhexyl, 2-propylpentyl, 2-methyl-3-ethylpentyl, 3-ethylheptyl, 1,3,5-trimethylhexyl, 1,5-dimethyl-4-ethylhexyl, 2-propylheptyl, 5-methyl-2-butylhexyl, 2-propylnonyl, 2-butyloctyl, 1,1-dimethylundecyl, 2-pentylnonyl, 1,2-dimethyltetradecyl, 1,1-dimethylpentadecyl and the like. Straight or branched-chain alkyl groups containing from 7 to 9 carbon atoms are preferred.

When R in the formulas herein is a cycloalkyl group containing from 5 to 7 carbon atoms, there are included cyclopentyl, cyclohexyl, cycloheptyl and the like.

When R in the formulas herein is phenyl substituted by methylenedioxy or one or two substituents selected from the group consisting of halogen, lower-alkyl, lower-alkoxy, nitro, cyano and trifluoromethyl, there are included p-chlorophenyl, o-chlorophenyl, m-chlorophenyl, p-bromophenyl, m-fluorophenyl, p- iodophenyl, 2,4-dichlorophenyl, 2,4-difluorophenyl, 2,5-dibromophenyl, 3,5-dichlorophenyhl, 3-chloro-4-fluorophenyl, 3,4-methylenedioxyphenyl, p-ethylphenyl, p-methoxyphenyl, m-nitrophenyl, o-cyanophenyl, m-(trifluoromethyl)phenyl, 2-methoxy-5-methylphenyl, and the like.

In the formulas herein R can also be benzyl. If desired, the phenyl moiety of the benzyl group can be substituted with from one to two substituents such as for example, halogen, hydroxy, lower-alkyl, lower-alkoxy, nitro, cyano, trifluoromethyl, and the like.

In Formula I, R is the same in both occurrences. $R_1$ is also the same in both its occurrences in Formula I.

When A in the formulas herein is an anion there are included anions of both inorganic and organic acids for example: bromide, chloride, fluoride, iodide, sulfate, phosphate, monofluorophosphate, nitrate, sulfamate, methanesulfonate, ethanesulfonate, benzenesulfonate, p-toluenesulfonate, naphthalenesulfonate, naphthalenedisulfonate, cyclohexylsulfamate, acetate, trifluoroacetate, malate, fumarate, succinate, tartrate, tartronate, oxalate, citrate, lactate, gluconate, ascorbate, lactate, phthalate, salicylate, benzoate, picrate, methanephosphate, ethane-1-hydroxy-1,1-diphosphonate, arsenite, arsenate, thiosulfate, perchlorate, sarcosinate, N-lauroylsarcosinate, nitrilotriacetate, 2-hydroxyethylnitrilodiacetate, zinc phenolsulfonate, 1-oxo-2-pyridinethiolate

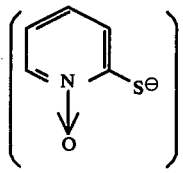

tetrafluoroborate, hexachloroplatinate, hexafluoroaluminate, tetrachloroaluminate, hexafluorostannate, hexachlorostannate, hexafluorosilicate, fluorozirconate and the like. Bromide and chloride are preferred.

The term "halogen" as used herein is intended to include fluorine, chlorine, bromine and iodine.

In the terms lower-alkyl and lower-alkoxy, "lower" denotes an alkyl moiety containing from 1 to 4 carbon atoms such as methyl, ethyl, propyl, isopropyl, butyl, isobutyl and tert-butyl.

The compounds of Formula I hereinabove are obtained by reacting a 4-(R-amino)pyridine having Formula II hereinbelow:

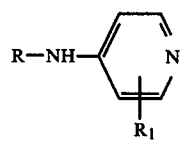

with a disubstituted alkane having Formula III hereinbelow:

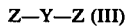

wherein in Formulas II and III R, $R_1$ and Y have the previously given meanings and Z is selected from the group consisting of chloro, bromo, iodo, methanesulfonyloxy, ethanesulfonyloxy, benzenesulfonyloxy and p-toluenesulfonyloxy.

The reaction is conveniently carried out by reacting two moles of a 4-(R-amino)pyridine (Formula II) with one mole of an appropriately disubstituted alkane (Formula III) in an inert solvent such as a lower alkanol, acetonitrile, N,N-dimethylformamide, N,N-dimethylacetamide, benzene, toluene, xylene and the like, at a temperature of from about 80° C. to 150° C. for a period of from 2 to 24 hours. Usually the reactants are heated at 80° C. to 100° C. in acetonitrile or N,N-dimethylformamide or a mixture of these solvents for about 15 to 20 hours.

Alternatively the reaction may be carried out in the absence of a solvent by heating stoichiometric quantities of the reactants at 120° C.-150° C. for about 2 to 5 hours.

The resulting bis-[4-(R-amino)-1-pyridinium]alkanes (Formula I) are isolated according to conventional methods, for example by filtration, if the product is insoluble in the reaction medium, or by dilution of the reaction mixture with a non-polar solvent such as ether, benzene or hexane in order to precipitate the product or by evaporation of the reaction medium to leave the product as a residue. The isolated crude product can be purified by crystallization from a suitable solvent in the presence of an adsorbent, e.g. charcoal or diatomaceous earth.

The bis-[4-(R-amino)-1-pyridinium]alkanes produced in accordance with the above-described method will, of course, contain an anion (A in Formula I) which corresponds to the leaving group of the reactant disubstituted alkane (Z in Formula III).

However, the anionic moiety of these compounds can be varied, if desired, according to conventional ion exchange methods, for example by passing a solution of a pyridinium compound in a suitable solvent, e.g. methanol, ethanol or water through a bed of synthetic ion exchange resin containing the desired anion. The solvent is evaporated and the resulting pyridinium compound containing the desired anion is purified by recrystallization from a suitable solvent.

Alternatively, a pyridinium compound can be reacted with a soluble salt containing the desired anion in association with a counter-cation which combines with the anion of the pyridinium compound to produce an insoluble precipitate. The latter is separated leaving a solution of the pyridinium compound containing the desired anion. For example a bis[4-(R-amino)-1-pyridinium]alkane dihalide is reacted with the silver salt of an organic or inorganic acid. The precipitated silver halide is removed leaving a solution of the pyridinium compound containing the desired organic or inorganic anion.

The above type of metathetical reaction can also be employed to prepare insoluble pyridinium compounds. Thus a soluble bis-[4-(R-amino)-1-pyridinium]alkane is reacted with a soluble salt containing the desired anion which combines with the pyridinium cation to afford the desired product as an insoluble precipitate. These insoluble pyridinium salts are useful for purposes of isolation and purification and when suitably composited as emulsions, creams, pastes, lotions, jellies or powders also serve as depot preparations providing slow, sustained release of the antimicrobial pyridinium compound. Moreover, insoluble salts derived from certain anions such as those described in U.S. Pat. No. 3,937,807, issued Feb. 10, 1976 are effective in reducing the tooth staining potential of dental plaque preventive agents.

Thus, should the anionic portion of a given compound accord to that species characteristics such as solubility, stability, molecular weight, physical appearance toxicity or the like, which render that form of the compound unsuitable for a desired purpose, it can readily be converted to another, more suitable form. For use on the skin or other tissues or in the oral cavity, pharmaceutically acceptable anions such as, fluoride, chloride, bromide, iodide, methanesulfonate, and the like, are of course employed.

The 4-(R-amino)pyridines (Formula II) which are used as starting materials generally are known or, if specifically new, are prepared according to the proceudres described for preparation of the known compounds.

Conveniently, the 4-(R-amino)pyridines are prepared by reacting 4-chloro or 4-bromopyridine or N-(4-pyridyl)-pyridinium chloride hydrochloride with an appropriately substituted amine. The reaction is usually carried out by heating the reactants in the absence of a solvent at 150° C.–225° C. for about 1.5 to 3 hours. The product is isolated in a conventional manner, for example by extraction from alkaline aqueous medium into an organic solvent such as ether, methylene chloride or chloroform, evaporation of the organic solvent and crystallization of the residue from an appropriate solvent.

Alternatively, the 4-(R-amino)pyridines are obtained by catalytic hydrogenation of a mixture containing 4-amino-pyridine and a carbonyl compound containing the appropriate carbon content. The reaction is usually carried out at a temperature of 50°–70° C. in a suitable solvent, for example ethanol, under a hydrogen pressure of 20–60 psi, in the presence of a palladium hydrogenation catalyst. A hydrogenation time of 4–10 hours is generally satisfactory. The use of a large excess of the carbonyl compound, i.e. 200% or greater advantageously results in high yields of pure product in a reaction time of 5 hours or less. Following removal of the catalyst the product is isolated by evaporation of the solvent and either distilling the residue or crystallizing the latter from a suitable solvent.

Reaction of an aldehyde having the appropriate carbon content with 4-aminopyridine in the presence of formic acid at elevated temperatures also provides the 4-(R-amino)pyridines.

The 4-(R-amino)pyridines can also be obtained by acylation of 4-aminopyridine with an acyl halide having the appropriate carbon content followed by reduction of the resulting amide. The acylation is carried out according to art-recognized methods, for example by reacting 4-aminopyridine with an acyl halide in an inert solvent such as methylene dichloride or chloroform in the presence of an acid acceptor such as triethylamine. The amide so-produced is then reduced with a complex metal hydride such as lithium aluminum hydride in a suitable solvent such as tetrahydrofuran, ether or dioxane and the amine product isolated in accordance with known procedures.

The disubstituted alkanes having Formula III also used as starting materials generally are known compounds, or if specifically new can be prepared according to the procedures used for preparing the known compounds.

As described more fully hereinbelow the compounds having Formula I exhibited in vitro antimicrobial activity against several species of microorganisms among which are included both gram positive and gram negative bacteria, several species of fungi and Herpes viruses. The compounds are therefore indicated for use as antimicrobial or antiseptic agents which can be applied topically to effect the degerming of human skin and other tissues and to sanitize and disinfect inanimate surfaces. Thus, the compounds can be used in topical antiseptic solutions for the treatment of wounds, in antibacterial cleansing agents such as surgical hand scrubs, patient pre-operative skin preparations, soaps, and shampoos, or in household and industrial cleaners, disinfectants and protective coverings such as paints, varnishes and waxes. The compounds are adapted for the above indicated utilities by combining them with conventional diluents or carriers, compatible cationic, anionic or non-ionic surfactants, buffering agents, perfumes and coloring agents, and are applied to a surface to be disinfected by conventional methods such as scrubbing, spraying, swabbing, immersion and the like.

For use as skin-cleansing agents the bis-[4-(R-amino)-1-pyridinium]alkanes can be prepared as liquids, or, if desired, the liquid formulations can be thickened by certain additives into a gel or paste or molded into a bar according to methods known in the art. For example, the compounds can be formulated with any compatible, pharmaceutically acceptable surfactant preferably a non-ionic surfactant such as the polyoxyethylene polyoxypropylene copolymers described in U.S. Pat. No. 3,855,140, amine oxides such as stearyl dimethyl amine oxide described in U.S. Pat. No. 3,296,145 and the like or with mixtures of these. The formulations may additionally contain pharmaceutically acceptable diluents such as water, lower alkanols and the like, acids, bases, or buffering agents so as to maintain a pH of 5.0 to 7.5, and, optionally, perfumes and coloring agents. The bis-[4-(R-amino)-1-pyridinium]alkane component of such formulations is generally present in a concentration of approximately 0.5 to 2.0 percent by weight, preferably 1.0 percent by weight.

When prepared as a tincture the bis-[4-(R-amino)1-pyridinium]alkanes may be formulated with water, a lower alkanone, e.g. acetone, and a lower alkanol such as ethanol. If desired the tincture may be tinted with a coloring agent. The active ingredient is generally present in a concentration of about 0.05 to 1.0 percent (w/v) preferably 0.1 percent (w/v).

Alternatively, the compounds can be formulated in suitable pharmaceutical vehicles for treating bacterial and fungal infections for example as lotions, ointments, or creams by incorporating them in conventional lotion, ointment or cream bases, such as alkyl polyether alcohols, cetyl alcohol, stearyl alcohol and the like, or as powders by incorporating them in conventional powder bases such as starch, talc and the like, or as jellies, by incorporating them in conventional jelly bases such as glycerol and tragacanth. They can also be formulated for use as aerosol sprays or foams.

When used for sanitizing and disinfecting inanimate surfaces the compounds can be formulated with known detergents and builders such as trisodium phosphate, borax and the like. The bis-[4-(R-amino)-1-pyridinium]alkane component of such formulations is generally present in a concentration up to about 10 percent by weight.

As described in detail hereinbelow certain of the compounds of Formula I are effective in preventing the formation of dental plaque. When intended for such use the compounds can conveniently be applied to the teeth in the form of a mouthwash or a dentifrice. The compounds can be composited with conventional ingredients used in mouthwash or dentifrice formulations, for example water, alcohol, glycerin, buffers, thickeners, flavoring and coloring agents. The bis-[4-(R-amino)-1-pyridinium]alkane is usually present in such formulations in a concentration of about 0.005 to 0.05 percent by weight preferably about 0.01 percent by weight.

It will of course be appreciated that the vehicles, diluents, carriers and additives contained in the above-described formulations are compatible with the active ingredient, i.e. the antimicrobial effectiveness of the bis-[4-(R-amino)-1-pyridinium]alkanes is not vitiated by effects ascribable to the nature of the vehicle, diluent, carrier or other additive.

The molecular structures of the compounds of the invention were assigned on the basis of study of their infrared and NMR spectra, and confirmed by the correspondence between calculated and found values for elemental analyses for the elements.

The invention is illustrated by the following examples without, however, being limited thereto.

EXAMPLE 1

A. A mixture containing 130 g. (0.67 mole) of 4-bromopyridine hydrochloride and 152 g. (1.0 mole) of n-heptylamine hydrochloride was heated in an oil bath. When the bath temperature reached 180°–185° C. the reaction mixture began to melt and stirring was begun. At 190°–195° C. melting was complete and the liquid mixture was stirred and heated at 210°–220° C. for 2.5 hours. The reaction mixture was then cooled to room temperature and the resulting solid was dissolved in water, made alkaline with 35% aqueous sodium hydroxide and the product extracted with chloroform. The chloroform extracts were dried over anhydrous sodium sulfate and evaporated to dryness under reduced pressure. The resulting viscous oil was diluted with a small amount of n-hexane and cooled to give a solid which was collected by filtration and air-dried to afford 86.6 g. of 4-(heptylamino)pyridine, m.p. 49°–51° C.

B. Alternatively, 4-(heptylamino)pyridine was prepared as follows: A mixture containing 229 g. (1.0 mole) of N-(4-pyridyl)pyridinium chloride hydrochloride and 228 g. (1.5 moles) of n-heptylamine hydrochloride was heated 2 hours with stirring in an oil bath at a bath temperature of 215° C. The reaction mixture was cooled to 80° C., diluted with ice-water, made alkaline with 35% aqueous sodium hydroxide and extracted successively with ether and chloroform. The organic extracts were combined and evaporated to dryness under reduced pressure. The residual viscous oil was dissolved in ether and the ethereal solution was washed with water. The aqueous wash was back-extracted with chloroform and the chloroform extracts were combined with the ethereal solution. The combined organic solutions were dried over anhydrous sodium sulfate and evaporated to dryness under reduced pressure. Cooling the residual oil to −78° C. effected partial solidification. The semi-solid was diluted with a small amount of ether and filtered. The solid so-obtained was dissolved in a mixture of acetonitrile and chloroform, the resulting solution treated with decolorizing carbon, filtered, and the filtrate evaporated to dryness under reduced pressure. The resulting semi-solid was diluted with a small amount of ether and cooled. The solid thus-produced was collected by filtration and washed with a small volume of cold ether to give, after drying, 84.6 g. of 4-(heptylamino)pyridine, m.p. 50°–52° C.

C. 4-(Heptylamino)pyridine was also prepared by hydrogenating a mixture containing 4-aminopyridine and heptaldehyde according to the procedure described in Example 9B hereinbelow.

D. To a stirred warm solution containing 10.0 g. (0.052 mole) of 4-(heptylamino)pyridine in 40 ml. of acetonitrile was added dropwise a solution containing 9.3 g. (0.026 mole) of 1,14-dibromotetradecane in 230 ml. of acetonitrile and the resulting mixture was heated 20 hours under reflux. The product which precipitated upon cooling the reaction mixture to room temperature was collected by filtration, washed with cold acetonitrile and dried affording 13.9 g. of 1,14-bis-[4-(heptylamino)-1-pyridinium]-tetradecane dibromide, m.p. 88°–90° C.

EXAMPLE 2

A solution containing 5.0 g. of 1,14-bis-[4-(heptylamino)-1-pyridinium]tetradecane dibromide in 5.0 ml. of methanol was added to the top of a 3-inch diameter column containing 500 ml. of synthetic anion exchange resin in the chloride form (sold by Rohm and Haas under the tradename Amberlite IRA 400) packed in methanol and eluted with five 125-ml. portions of methanol. The combined eluate was evaporated to dryness under reduced pressure and the residual oil was redissolved in ethanol, treated with decolorizing carbon and evaporated to dryness. The residual solid was triturated with ether containing a few drops of acetonitrile, collected by filtration and dried over phosphorus pentoxide under vacuum to give 3.94 g. of 1,14-bis-[4-(heptylamino)-1-pyridinium]tetradecane dichloride, m.p. 113°–116° C.

EXAMPLE 3

A stirred suspension containing 11.54 g. (0.06 mole) of 4-(heptylamino)pyridine in 75 ml. of acetonitrile was heated under reflux until a clear homogeneous solution was formed. To the clear solution was then added dropwise a warm solution containing 9.84 g. (0.03 mole) of 1,12-dibromododecane in 75 ml. of acetonitrile. When the addition was complete, heating under reflux was continued 18 hours. After cooling to room temperature, the reaction mixture was evaporated to dryness under reduced pressure. The residual solid was slurried in ether, collected by filtration and dried 48 hours under vacuum at 60° C. to afford 21.1 g. of 1,12-bis-[4-(heptylamino)-1-pyridinium]dodecane dibromide, m.p. 101°–103° C.

EXAMPLE 4

A. A solution containing 6.6 g. of 1,12-bis-[4-(heptylamino)-1-pyridinium]dodecane dibromide in 25 ml. of methanol was added to the top of a 3-inch diameter column packed with 1 liter of synthetic anion exchange resin in the chloride form (sold by Rohm and Haas under the tradename Amberlite IRA 400) in methanol and eluted slowly with 100-ml. portions of methanol until 700 ml. of eluate had been collected. The combined eluate was evaporated to dryness under reduced pressure below 25° C. The residual gum was triturated repeatedly with a 6 to 1 mixture of ether and acetonitrile and dried under vacuum to afford 5.0 g. of 1,12-bis-[4-(heptylamino)-1-pyridinium]dodecane dichloride, m.p. 109°–112° C.

B. Alternatively, a mixture containing 76.8 g. (0.4 mole) of 4-(heptylamino)pyridine and 47.8 g. (0.2 mole) of 1,12-dichlorododecane was heated 4 hours at 125°–130° C. After slight cooling 300 ml. of acetonitrile was added and the resulting mixture was heated at steam bath temperature to effect complete solution then stored in a refrigerator overnight. The precipitated product was collected by filtration, washed with cold acetonitrile and ether, and the hygroscopic product immediately dried under vacuum to give 112 g. of 1,12-bis-[4-(heptylamino)-1-pyridinium]dodecane dichloride, m.p. 112°–115° C.

EXAMPLE 5

A. A mixture containing 100.0 g. (0.51 mole) of 4-bromopyridine hydrochloride and 110 g. (0.8 mole) of n-hexylamine hydrochloride was heated in an oil bath. When the bath temperature reached 175°–180° C. the reaction mixture began to melt and stirring was begun. The temperature of the bath was then raised to 227° C. and the stirring continued 3.5 hours. After cooling to room temperature the reaction mixture was dissolved in hot water, the resulting solution cooled with ice, made alkaline with dilute aqueous sodium hydroxide and extracted with chloroform. The chloroform extracts were dried over anhydrous sodium sulfate and evaporated to dryness under reduced pressure. The residue was triturated with ether and cooled. The resulting solid was collected by filtration and washed with cold ether. Evaporation of the filtrate afforded a second crop of solid. The crops were combined, dissolved in chloroform, treated with decolorizing carbon and filtered. The filtrate was evaporated under reduced pressure, and the residue was triturated with cold ether. The product thus-obtained was collected by filtration, washed with cold ether and dried to give 63.6 g. of 4-(hexylamino)pyridine, m.p. 66°–68° C. Evaporation of the filtrate afforded an additional 7.0 g., m.p. 65°–67° C.

B. Alternatively, 4-(hexylamino)pyridine was prepared as follows. A mixture containing 229 g. (1 mole) of N-(4-pyridyl)pyridinium chloride hydrochloride and 207 g. (1.5 moles) of n-hexylamine hydrochloride was stirred and heated 1.75 hours at 175°–185° C. The reaction was cooled and diluted with 750 ml. of ice-water. The resulting solution was made alkaline with 35% aqueous sodium hydroxide and after further dilution with 1 l. of water was extracted with ether followed by dichloromethane. The organic extracts were combined, dried over anhydrous sodium sulfate and evaporated to dryness under reduced pressure. The residue was crystallized from ether, redissolved in chloroform, the resulting solution treated with decolorizing carbon and filtered. The filtrate was evaporated to dryness under reduced pressure and the residue was triturated with a mixture of ether and acetonitrile. The solid thus-obtained was again dissolved in chloroform and the resulting solution treated with decolorizing carbon and filtered. The filtrate was evaporated to dryness under reduced pressure and the residue was triturated with cold ether to give 71.0 g. of 4-(hexylamino)pyridine, m.p. 68°–70° C.

C. To a stirred warm solution containing 10.7 g. (0.06 mole) of 4-(hexylamino)pyridine in 50 ml. of acetonitrile was added dropwise a solution containing 10.7 g. (0.03 mole) of 1,14-dibromotetradecane in 250 ml. of acetonitrile and the resulting mixture heated 22 hours under reflux. The reaction was then evaporated to dryness under reduced pressure. The residual solid was dissolved in acetonitrile and the resulting solution treated with decolorizing carbon and filtered. The filtrate was evaporated to dryness under reduced pressure and the resulting oil crystallized from acetonitrile. The product was collected by filtration and dried 48 hours at 70° C./0.1 mm. to give 13.4 g. of 1,14-bis-[4-(hexylamino)-1-pyridinium]tetradecane dibromide, m.p. 91°–93° C.

EXAMPLE 6

Following a procedure similar to that described in Example 2 but employing 5.0 g. of 1,14-bis-[4-(hexylamino)-1-pyridinium]tetradecane dibromide there was obtained 4.33 g. of the corresponding dichloride, m.p. 94°–95° C.

EXAMPLE 7

Following a procedure similar to that described in Example 5C but employing 10.7 g. (0.06 mole) of 4-(hexylamino)pyridine and 9.85 g. (0.03 mole) of 1,12-dibromododecane there was obtained 17.6 g. of 1,12-bis-[4-(hexylamino)-1-pyridinium]dodecane dibromide, m.p. 122°–124° C.

EXAMPLE 8

Following a procedure similar to that described in Example 2 but employing 5.0 g. of 1,12-bis-[4-(hexylamino)-1-pyridinium]dodecane dibromide there was obtained 3.69 g. of the corresponding dichloride, m.p. 86°–88° C.

EXAMPLE 9

A. A mixture containing 183.3 g. (0.8 mole) of N-(4-pyridyl)pyridinium chloride hydrochloride and 162 g. (0.98 mole) of n-octylamine hydrochloride was heated in an oil bath to a bath temperature of 225°–230° C. (internal temperature of 188° C.) and the resulting liquid was stirred at that temperature for 2.5 hours. The reaction mixture was then cooled to 70° C., diluted with 1 liter of ice and water, made alkaline with 35% aqueous sodium hydroxide and extracted with chloroform. The chloroform extracts were dried over anhydrous sodium sulfate, treated with decolorizing carbon and evaporated to dryness under vacuum. The resulting oil was cooled to −78° C. The semi-solid which formed was triturated with ether and the solid thus-obtained collected by filtration, washed with cold ether and dried. The filtrate afforded a second crop of 10 g. The crops were combined, dissolved in chloroform and, following treatment with decolorizing carbon and filtration (repeated 3 times), the chloroform solution was evaporated to dryness under reduced pressure. The resulting solid was triturated with ether, cooled, collected by filtration and washed with cold ether-hexane to give 63.3 g. or nearly colorless 4-(octylamino)pyridine, m.p. 62°–63° C.

B. Alternatively 4-(octylamino)pyridine was prepared as follows: A mixture containing 94 g. (1 mole) of 4-aminopyridine, 384 g. (3 moles) of octaldehyde, 7 g. of 10% palladium-on-carbon hydrogenation catalyst and sufficient absolute ethanol to give a total volume of 1.2 l. was hydrogenated 4.5 hours at 70°–90° C. under an initial hydrogen pressure of 45 psi. After cooling the mixture the hydrogenation catalyst was removed by filtration and the filtrate was evaporated to dryness under reduced pressure. The residual oil crystallized on standing and the solid product was triturated with hexane, collected by filtration, washed with fresh hexane and dried at 40° C. under vacuum to give 182 g. of 4-(octylamino)pyridine, m.p. 70°–73° C.

C. In another preparation a finely ground mixture containing 500 g. (3.33 moles) of 4-chloropyridine hydrochloride and 55 g. (3.33 moles) of octylamine hydrochloride was gradually heated to an internal temperature of 180° C. in a nitrogen atmosphere and vigorous stirring was begun as soon as it became possible. The temperature was gradually increased to 205° C. over 2–3 hours and then maintained for 7 hours. The reaction mixture was allowed to cool and approximately 2 liters of boiling water was added as soon as the dark melt began to crystallize. The resulting solution was cooled, made alkaline with 35% sodium hydroxide and extracted with dichloromethane. The organic extracts were washed with water, dried over anhydrous sodium sulfate and evaporated to dryness. The residual solid was treated with 700 ml. of boiling hexane, cooled, filtered and washed with cold hexane to give 641 g. of air-dried 4-(octylamino)pyridine, m.p. 66°–69° C.

D. To a stirred, warm solution containing 10.0 g. (0.049 mole) of 4-(octylamino)pyridine in 150 ml. of acetonitrile was added dropwise a solution containing 7.4 g. (0.0245 mole) of 1,10-dibromodecane in 50 ml. of acetonitrile and the resulting mixture heated 18 hours under reflux. After cooling and stirring 1 hour at room temperature, the precipitated solid was collected by filtration, washed with acetonitrile and dried 48 hours at 85° C. to give 15.6 g. of 1,10-bis-[4-(octylamino)-1-pyridinium]decane dibromide, m.p. 163°–164° C.

EXAMPLE 10

A. Following a procedure similar to that described in Example 2 but employing 5.0 g. of 1,10-bis-[4-(octylamino)-1-pyridinium]decane dibromide there was obtained 4.31 g. of the corresponding dichloride, m.p. 213°–214° C.

B. Alternatively, a mixture containing 61.8 g. of 4-(octylamino)pyridine and 31.5 g. of 1,10-dichlorodecane was stirred and heated slowly to 120° C. The heat source was removed and the temperature of the now exothermic reaction continued to rise to 180° C. As soon as the reaction mixture began to crystallize 250 ml. of N,N-dimethylformamide was rapidly added and the resulting mixture was heated to give a clear homogeneous solution and then cooled to 0° C. The precipitated product was collected by filtration, washed with ether and dried 24 hours under vacuum at 60° C. to give 73 g. of 1,10-bis-[4-(octylamino)-1-pyridinium]decane dichloride, m.p. 215°–217° C.

C. To a stirred, filtered solution containing 9.8 g. (0.0157 mole) of the above dichloride in 200 ml. of distilled water under nitrogen was added dropwise 14.9 g. (equivalent to 5.96 g. or 0.04 mole) of 40% sodium 1-oxo-2-pyridinethiolate. The resulting precipitate was collected, washed with water, and dried over phosphorus pentoxide under vacuum affording 10.7 g. of 1,10-bis-[4-(octylamino)-1-pyridinium]decane bis(1-oxo-2-pyridinethiolate) as a pale yellow solid, m.p. 134°–137° C.

EXAMPLE 11

Following a procedure similar to that described in Example 9D but employing 11.1 g. (0.054 mole) of 4-(octylamino)pyridine and 7.34 g. (0.027 mole) of 1,8-dibromooctane, and heating the reaction mixture 6 hours under reflux there was obtained 15.6 g. of 1,8-bis-[4-(octylamino)-1-pyridinium]octane dibromide, m.p. 174°–175° C.

EXAMPLE 12

Following a procedure similar to that described in Example 2 but employing 5.0 g. of 1,8-bis-[4-(octylamino)-1-pyridinium]octane dibromide there was obtained 4.30 g. of the corresponding dichloride, m.p. 210°–211° C.

EXAMPLE 13

Following a procedure similar to that described in Example 9D but employing 11.1 g. (0.054 mole) of 4-(octylamino)pyridine and 6.6 g. (0.027 mole) of 1,6-dibromohexane and heating the reaction mixture 9 hours under reflux there was obtained 15.1 g. of 1,6-bis-[4-(octylamino)-1-pyridinium]hexane dibromide, m.p. 136°–138° C.

EXAMPLE 14

Following a procedure similar to that described in Example 2 but employing 5.0 g. of 1,6-bis-[4-(octylamino)-1-pyridinium]hexane dibromide there was obtained 4.23 g. of the corresponding dichloride, m.p. 189°–191° C.

EXAMPLE 15

To a stirred warm solution containing 2.06 g. (0.01 mole) of 4-(octylamino)pyridine in 15 ml. of acetonitrile was added dropwise a solution containing 1.37 g. (0.005 mole) of 1,6-hexanediol dimethanesulfonate in 10 ml. of acetonitrile and the resulting mixture was heated under reflux 20 hours. The reaction mixture was evaporated to dryness under reduced pressure and the residual gum was triturated with ether to give a colorless hygroscopic solid. This product was redissolved in a mixture of ethanol, benzene and acetonitrile and the resulting solution evaporated to dryness under reduced pressure. The residue was triturated with ether and the resulting white solid was quickly collected by filtration, washed with anhydrous ether, and dried 72 hours at 28° C./0.1 mm. to give 2.65 g. of 1,6-bis[4-(octylamino)-1-pyridinium]hexane dimethanesulfonate as a waxy, white solid.

EXAMPLE 16

Following a procedure similar to that described in Example 9D but employing 14.24 g. (0.08 mole) of 4-(hexylamino)pyridine and 8.64 g. (0.04 mole) of 1,4-dibromobutane there was obtained following trituration of the crude product with a mixture of acetonitrile and acetone 20.45 g. of 1,4-bis-[4-(hexylamino)-1-pyridinium]butane dibromide, m.p. 199°–201° C.

EXAMPLE 17

Following a procedure similar to that described in Example 9D but employing 10.7 g. (0.06 mole) of 4-(hexylamino)pyridine and 7.32 g. (0.03 mole) of 1,6-dibromohexane there was obtained following trituration of the crude product with a mixture of ether, acetonitrile and acetone 14.90 g. of 1,6-bis-[4-(hexylamino)-1-pyridinium]-hexane dibromide, m.p. 178°–179° C.

EXAMPLE 18

Following a procedure similar to that described in Example 9D but employing 10.7 g. (0.06 mole) of 4-(hexylamino)pyridine and 7.75 g. (0.03 mole) of 1,7-dibromoheptane there was obtained following trituration of the crude product with a mixture of acetonitrile and acetone 16.4 g. of 1,7-bis-[4-(hexylamino)-1-pyridinium]heptane dibromide, m.p. 157°–158° C.

EXAMPLE 19

Following a procedure similar to that described in Example 9D but using 10.7 g. (0.06 mole) of 4-(hexylamino)-pyridine and 8.6 g. (0.03 mole) of 1,9-dibromononane there was obtained 17.15 g. of 1,9-bis-[4-(hexylamino)-1-pyridinium]-nonane dibromide, m.p. 114°–115° C.

EXAMPLE 20

Following a procedure similar to that described in Example 9D but employing 15.4 g. (0.08 mole) of 4-(heptylamino)pyridine and 8.64 g. (0.04 mole) of 1,4-dibromobutane there was obtained 23.1 g. of 1,4-bis-[4-(heptylamino)-1-pyridinium]butane dibromide, m.p. 229°–230° C.

EXAMPLE 21

Following a procedure similar to that described in Example 9D but employing 10.0 g. (0.052 mole) of 4-(heptylamino)pyridine and 6.7 g. (0.026 mole) of 1,7-dibromoheptane there was obtained 14.05 g. of 1,7-bis-[4-(heptylamino)-1-pyridinium]heptane dibromide, m.p. 142°–143° C.

EXAMPLE 22

Following a procedure similar to that described in Example 9D but employing 11.6 g. (0.06 mole) of 4-(heptylamino)pyridine and 8.2 g. (0.03 mole) of 1,8-dibromoctane there was obtained after recrystallization from acetonitrileether 18.6 g. of 1,8-bis-[4-(heptylamino)-1-pyridinium]-octane dibromide, m.p. 161°–162° C.

EXAMPLE 23

Following a procedure similar to that described in Example 2 but employing 5.0 g. (0.0076 mole) of 1,8-bis[4-(heptylamino)-1-pyridinium]octane dibromide there was obtained 4.1 g. of the corresponding dichloride, m.p. 206°–208° C.

EXAMPLE 24

Following a procedure similar to that described in Example 9D but employing 15.4 g. (0.08 mole) of 4-(heptylamino)pyridine and 11.44 g. of 1,9-dibromomononane there was obtained 21.3 g. of 1,9-bis-[4-(heptylamino)-1-pyridinium]nonane dibromide, m.p. 115°–116° C.

EXAMPLE 25

Following a procedure similar to that described in Example 2 but employing 5.0 g. (0.0075 mole) of 1,9-bis[4-(heptylamino)-1-pyridinium]nonane dibromide there was obtained 4.2 g. of the corresponding dichloride, m.p. 154°–155° C.

EXAMPLE 26

Following a procedure similar to that described in Example 9D but employing 15.4 g. (0.08 mole) of 4-(heptyl-amino)pyridine and 12.0 g. (0.04 mole) of 1,10-dibromodecane there was obtained 25.7 g. of 1,10-bis-[4-(heptylamino)-1-pyridinium]decane dibromide, m.p. 163°–165° C.

EXAMPLE 27

Following a procedure similar to that described in Example 2 but employing 5.0 g. (0.0073 mole) of 1,10-bis-[4-(heptylamino)-1-pyridinium]decane dibromide there was obtained 4.35 g. of the corresponding dichloride, m.p. 209°–210° C.

EXAMPLE 28

To a stirred slurry of 30 ml. of synthetic anion exchange resin in the hydroxide form (sold by Rohm and Haas under the tradename Amberlite IRA 400) in 150 ml. of water was added dropwise 48% aqueous hydrofluoric acid until the mixture was acidic. After stirring an additional 0.5 hour the slurry was poured into a column. The column was drained and the resin washed with a solution containing 15 ml. of 48% aqueous hydrofluoric acid in 185 ml. of distilled water. The resin was then washed with distilled water until the eluate was weakly acidic, and then successively with 20%, 40%, and 50% aqueous methanol and finally with absolute methanol until the eluate was neutral. To the top of this column of ion exchange resin now in the fluoride form was added a solution containing 0.25 g. (0.000365 mole) of 1,10-bis-[4-heptylamino)-1-pyridinium]decane dibromide in 1 ml. of methanol. Five fractions of 15 ml. each were collected. The first three fractions were combined and evaporated to dryness under reduced pressure. The oily residue was dissolved in a mixture of toluene and ethanol and the resulting solution evaporated to dryness under reduced pressure. The residual oil was redissolved in a mixture of benzene and acetone and the solution concentrated to a small volume. The solid which separated was collected by filtration and dried 24 hours at 24° C./0.1 mm. to give 0.11 g. of impure 1,10-bis-[4-(heptylamino)-1-pyridinium]decane difluoride, m.p. 85°–90° C.

EXAMPLE 29

A. A solid mixture containing 115 g. (0.5 mole) of N-(4-pyridyl)pyridinium chloride hydrochloride and 119 g. (0.66 mole) of n-nonylamine hydrochloride was heated in an oil bath up to a bath temperature of 220° C. (internal temperature of 190°–194° C.) and the resulting liquid was stirred at that temperature for 2 hours. The reaction mixture was then cooled to 80° C., diluted with 1,2 liters of ice and water, made alkaline with 35% aqueous sodium hydroxide and extracted with chloroform. The chloroform extracts were dried over anhydrous sodium sulfate, treated with decolorizing carbon, filtered and evaporated to dryness under reduced pressure. The residual viscous oil was cooled to −78° C. and triturated with ether. The resulting solid was collected by filtration and washed with cold ether. The filtrate afforded a second crop of solid. The combined crops were redissolved in chloroform and the resulting solution treated with decolorizing carbon and filtered. This was repeated once more and the filtrate was then evaporated to dryness under reduced pressure. The residual semi-solid was triturated with ether and cooled to give a nearly colorless solid which was collected by filtration, washed with cold ether and dried. The solid was taken up in chloroform and the resulting solution treated with decolorizing carbon, filtered and evaporated to dryness under reduced pressure. Cooling the semi-solid so-obtained and trituration with ether afforded a colorless solid which was collected by filtration, washed with cold ether and dried to give 51.7 g. of 4-(nonylamino)pyridine, m.p. 59°–60° C. The filtrate afforded a second crop of 11.6 g., m.p. 55°–57° C.

B. Alternatively 4-(nonylamino)pyridine was prepared as follows: A mixture containing 39.5 g. (0.42 mole) of 4-aminopyridine, 175 g. (1.24 moles) of nonyl aldehyde, 5.0 g. of 10% palladium-on-carbon hydrogenation catalyst and sufficient absolute ethanol to give a total volume of 600 ml. was warmed and hydrogenated under an initial hydrogen pressure of 45 psi until the absorption of hydrogen ceased. The reaction mixture was filtered to remove the catalyst and the filtrate was evaporated to dryness under reduced pressure. The residual oil was then vacuum distilled to remove any nonyl alcohol which may have been produced. A fraction boiling at 63°-64° C./4.5 mm. was collected and set aside. The residue was triturated with ether and cooled at −78° C. The solid which precipitated was collected by filtration and washed with cold ether. This product was dissolved in chloroform, the resulting solution treated with decolorizing carbon, filtered and the filtrate evaporated to dryness. The residue was triturated with ether and cooled to −78° C. The solid thus-obtained was collected by filtration, washed with cold ether and air-dried to give 27.0 g. of 4-(nonylamino)-pyridine, m.p. 57°-59° C.

C. A stirred suspension of 11.0 g. (0.05 mole) of 4-(nonylamino)pyridine in 150 ml. of acetonitrile was warmed until a clear homogenous solution was obtained. To this clear solution was added dropwise a solution containing 6.8 g. (0.025 mole) of 1,8-dibromooctane in 50 ml. of acetonitrile and the resulting mixture heated 19 hours under reflux during which time a solid precipitated from solution. After cooling, the solid was collected by filtration, redissolved in methanol, the resulting solution treated with decolorizing carbon, filtered and evaporated to dryness under reduced pressure. Trituration of the residual oil with ether containing a small amount of acetonitrite produced a colorless crystalline solid which was collected by filtration and dried to give 15.5 g. of 1,8-bis-[4-(nonylamino)-1-pyridinium]octane dibromide, m.p. 178°-179° C.

EXAMPLE 30

Following a procedure similar to that described in Example 29C but employing 3.54 g. (0.026 mole) of 4-(propylamino)pyridine and 3.90 g. (0.013 mole) of 1,10-dibromodecane there was obtained 5.19 g. of 1,10-bis-[4-(propylamino)-1-pyridinium]decane dibromide, m.p. 206°-207° C.

EXAMPLE 31

Following a procedure similar to that described in Example 29C but employing 14.24 g. (0.08 mole) of 4-(hexylamino)pyridine and 9.20 g. (0.04 mole) of 1,5-dibromopentane there was obtained following recrystallization from acetonitrile-acetone 12.3 g. of 1,5-bis-[4-(hexylamino)-1-pyridinium]pentane dibromide, m.p. 155°-156° C.

EXAMPLE 32

Following a procedure similar to that described in Example 29C but employing 10.7 g. (0.06 mole) of 4-(hexylamino)pyridine and 8.2 g. (0.03 mole) of 1,8-dibromooctane there was obtained 16.3 g. of 1,8-bis-[4-(hexylamino)-1-pyridinium]octane dibromide, m.p. 180°-181° C.

EXAMPLE 33

Following a procedure similar to that described in Example 29C but employing 12.5 g. (0.07 mole) of 4-(hexylamino)pyridine and 10.5 g. (0.035 mole) of 1,10-dibromodecane there was obtained 16.0 g. of 1,10-bis-[4-(hexylamino)-1-pyridinium]decane dibromide, m.p. 148°-149° C.

EXAMPLE 34

Following a procedure similar to that described in Example 29C but employing 13.4 g. (0.076 mole) of 4-(cyclohexylamino)pyridine and 8.2 g. (0.038 mole) of 1,4-dibromobutane there was obtained 18.2 g. of 1,4-bis-[4-(cyclohexylamino)-1-pyridinium]butane dibromide, m.p. 288°-290° C.

EXAMPLE 35

Following a procedure similar to that described in Example 29C but employing 13.4 g. (0.076 mole) of 4-(cyclohexylamino)pyridine and 8.75 g. (0.038 mole) of 1,5-dibromopentane there was obtained 19.0 g. of 1,5-bis-[4-(cyclohexylamino)-1-pyridinium]pentane dibromide, m.p. 255°-256° C.

EXAMPLE 36

Following a procedure similar to that described in Example 29C but employing 13.4 g. (0.076 mole) of 4-(cyclohexylamino)pyridine and 9.3 g. (0.038 mole) of 1,6-dibromohexane there was obtained 19.1 g. of 1,6-bis-[4-(cyclohexylamino)-1-pyridinium]hexane dibromide, m.p. 307°-308° C.

EXAMPLE 37

Following a procedure similar to that described in Example 29C but employing 13.4 g. (0.076 mole) of 4-(cyclohexylamino)pyridine and 9.8 g. of (0.038 mole) of 1,7-dibromoheptane there was obtained 2.01 g. of 1,7-bis-[4-(cyclohexylamino)-1-pyridinium]heptane dibromide, m.p. 311°-313° C.

EXAMPLE 38

Following a procedure similar to that described in Example 29C but employing 13.4 g. (0.076 mole) of 4-(cyclohexylamino)pyridine and 10.34 g. (0.038 mole) of 1,8-dibromooctane there was obtained 19.1 g. of 1,8-bis-[4-(cyclohexylamino)-1-pyridinium]octane dibromide, m.p. 270°-271° C.

EXAMPLE 39

Following a procedure similar to that described in Example 29C but employing 13.4 g. (0.076 mole) of 4-(cyclohexylamino)pyridine and 10.8 g. (0.038 mole) of 1,9-dibromononane there was obtained 16.3 g. of 1,9-bis-[4-(cyclohexylamino)-1-pyridinium]nonane dibromide, m.p. 149°-151° C.

EXAMPLE 40

Following a procedure similar to that described in Example 29C but employing 13.4 g. (0.076 mole) of 4-(cyclohexylamino)pyridine and 11.4 g. (0.038 mole) of 1,10-dibromodecane there was obtained 19.0 g. of 1,10-bis-[4-(cyclohexylamino)-1-pyridinium]decane dibromide, m.p. 226°-227° C.

EXAMPLE 41

A. A mixture containing 298.0 g. (1.33 moles) of N-(4-pyridyl)pyridinium chloride hydrochloride and 322 g. (2 moles) of 2-ethylhexylamine hydrochloride was heated 2 hours with stirring in an oil bath at a bath temperature of 215° C. The mixture was cooled to 60° C., diluted with 500 ml. of water and kept cold by the addition of ice while being made alkaline with 35% aqueous sodium hydroxide. The alkaline mixture was extracted with ether and the ethereal extracts were dried over anhydrous sodium sulfate and evaporated to dryness. The residual oil was distilled under reduced pressure to give 101.0 g. of 4-(2-ethylhexylamino)pyridine b.p. 145°-150° C./0.9 mm.

B. Alternatively 4-(2-ethylhexylamino)pyridine was prepared as follows:

To a stirred solution containing 800 g. (8.4 moles) of 4-aminopyridine and 1500 ml. of triethylamine in 6.4 l. of dichloromethane there was added over 3 hours a solution containing 1610 g. (10.0 moles) of 2-ethylhexanoyl chloride in 1.6 l. of dichloromethane. Throughout the addition the temperature was maintained at 15° C. When the addition was complete the mixture was warmed on a steam bath 2 hours. After cooling the reaction mixture was washed thoroughly with water, dried over anhydrous sodium sulfate, treated with decolorizing carbon and filtered. Evaporation of the filtrate afforded 1843 g. of N-(4-pyridyl)-2-ethylhexanamide.

To a mixture containing 100 g. (2.63 moles) of lithium aluminum hydride in 2 l. of tetrahydrofuran was added at a sufficient rate to maintain gentle reflux a solution containing 570 g. (2.62 moles) of N-(4-pyridyl)-2-ethylhexanamide in 4 l. of tetrahydrofuran. When the addition was complete (approximately 3 hours) the reaction mixture was heated under reflux 7 hours. After cooling, the mixture was treated successively with 100 ml. of water, 100 ml. of 15% aqueous sodium hydroxide and 300 ml. of water. The solids were removed by filtration and the solvent was evaporated from the filtrate under reduced pressure. The residual oil was combined with the product of a duplicate run and vacuum distilled to give 837 g. of 4-(2-ethylhexylamino)pyridine b.p. 135°-160° C./0.2 mm.

C. To a stirred, warm solution containing 10.3 g. (0.05 mole) of 4-(2-ethylhexylamino)pyridine in 50 ml. of acetonitrile was added dropwise a solution containing 8.2 g. (0.025 mole) of 1,12-dibromodecane in 170 ml. of acetonitrile and the resulting mixture was heated 20 hours under reflux. Upon cooling to 0° C. a first crop of product precipitated and was cooled by filtration. Evaporation of the filtrate and trituration of the residue with ether afforded a second crop. The combined crops were dissolved in methanol, the resulting solution treated with decolorizing carbon, filtered and the filtrate evaporated to dryness under reduced pressure. The residual oil was cooled and triturated with ether to give a slightly discolored solid. Recrystallization from acetonitrile-ether followed by trituration of the product with ether followed by acetonitrile afforded, after drying 72 hours under vacuum at 60° C., 14.7 g. of 1,12-bis-[4-(2-ethylhexylamino)-1-pyridinium]dodecane dibromide as colorless granules, m.p. 146°14 147° C.

EXAMPLE 42

A. A mixture containing 353.5 g. (1.72 mole) of 4-(2-ethylhexylamino)pyridine and 205 g. (0.86 mole) of 1,12-dichlorododecane was heated to 120° C. The heat source was removed and the temperature of the now exothermic reaction continued to rise to 180°-190° C. When the temperature dropped to 135° C. one liter of acetonitrile was carefully added and the mixture heated under reflux to give a clear solution. The hot acetonitrile solution was combined with similar solutions from two other runs, treated with decolorizing carbon and filtered. The filtrate was cooled and the precipitated product was collected by filtration and washed with cold acetonitrile. Two recrystallizations from acetonitrile afforded 970 g. of 1,12-bis-[4-(2-ethylhexylamino)-1-pyridinium]dodecane dichloride, m.p. 168°-171° C.

B. Alternatively, by following a procedure similar to that described in Example 2 but employing 3.0 g. (0.00405 mole) of 1,12-bis-[4-(2-ethylhexylamino)-1-pyridinium]-dodecane dibromide there was obtained 2.0 g. of the corresponding dichloride, m.p. 172°-173° C.

EXAMPLE 43

Following a procedure similar to that described in Example 41C but employing 10.3 g. (0.05 mole) of 4-(octylamino)pyridine and 6.45 g. (0.025 mole) of 1,7-dibromoheptane there was obtained 14.85 g. of 1,7-bis-[4-(octylamino)-1-pyridinium]heptane dibromide, m.p. 129°-131° C.

EXAMPLE 44

A. Following a procedure similar to that described in Example 41C but using 11.1 g. (0.054 mole) of 4-(octylamino)pyridine and 7.72 g. (0.027 mole) of 1,9-dibromononane there was obtained 17.0 g. of 1,9-bis-[4-(octylamino)-1-pyridinium]nonane dibromide, m.p. 117°-119° C.

B. The corresponding dichloride prepared according to the procedure of Example 2 had a m.p. 161°-162° C.

EXAMPLE 45

Following a procedure similar to that described in Example 41C but employing 10.3 g. (0.05 mole) of 4-(octylamino)-pyridine and 8.2 g. (0.025 mole) of 1,12-dibromododecane there was obtained 15.2 g. of 1,12-bis-[4-(octylamino)-1-pyridinium]dodecane dibromide, m.p. 119°-120° C.

EXAMPLE 46

Following a procedure similar to that described in Example 41C but using 5.8 g. (0.028 mole) of 4-(octylamino)pyridine and 5.0 g. (0.014 mole) of 1,14-dibromotetradecane there was obtained 9.3 g. of 1,14-bis-[4-(octylamino)-1-pyridinium]tetradecane dibromide, m.p. 113°-115° C.

EXAMPLE 47

Following a procedure simolar to that described in Example 41C but employing 11.0 g. (0.05 mole) of 4-(nonylamino)-pyridine and 6.1 g. (0.025 mole) of 1,6-dibromohexane there was obtained 15.2 g. of 1,6-bis-[4-(nonylamino)-1-pyridinium]-hexane dibromide, m.p. 152°-154° C.

EXAMPLE 48

Following a procedure similar to that described in Example 4 but employing 6.5 g. (0.0095 mole) of 1,6-bis-[4-(nonylamino)-1-pyridinium]hexane dibromide there was obtained 4.95 g. of the corresponding dichloride, m.p. 194°-195° C.

EXAMPLE 49

Following a procedure similar to that described in Example 41C but employing 8.8 g. (0.04 mole) of 4-(nonylamino)pyridine and 5.2 g. (0.02 mole) of 1,7-dibromoheptane there was obtained 12.2 g. of 1,7-bis-[4-(nonylamino)-1-pyridinium]heptane dibromide, m.p. 132°-134° C.

EXAMPLE 50

Following a procedure similar to that described in Example 41C but employing 11.0 g. (0.05 mole) of 4-(nonylamino)pyridine and 7.15 g. (0.025 mole) of 1,9-dibromononane there was obtained 15.7 g. of 1,9-bis-[4-(nonylamino)-1-pyridinium]nonane dibromide, m.p. 121°–122° C.

EXAMPLE 51

Following a procedure similar to that described in Example 41C but employing 11.0 g. (0.05 mole) of 4-(nonylamino)pyridine and 7.5 g. (0.025 mole) of 1,10-dibromodecane there was obtained 15.63 g. of 1,10-bis-[4-(nonylamino)-1-pyridinium]decane dibromide, m.p. 172°–173° C.

EXAMPLE 52

Following a procedure similar to that described in Example 41C but employing 10.12 g. (0.046 mole) of 4-(nonylamino)pyridine and 7.54 g. (0.023 mole) of 1,12-dibromododecane there was obtained 16.4 g. of 1,12-bis-[4-(nonylamino)1-pyridinium]dodecane dibromide, m.p. 105°–106° C.

EXAMPLE 53

To a stirred, warm solution containing 12.4 g. (0.06 mole) of 4-(2-ethylhexylamino)pyridine in 100 ml. of acetonitrile was added dropwise a solution containing 6.9 g. (0.03 mole) of 1,5-dibromopentane in 25 ml. of acetonitrile and the resulting solution heated 20 hours under reflux. The reaction mixture was cooled and diluted with ether until slightly cloudy. Further cooling and stirring afforded a solid precipitate which was collected by filtration and washed with a cold mixture of acetonitrile and ether. The solid thus-obtained was dissolved in ethanol and the resulting solution treated with decolorizing carbon and filtered. Evaporation of the filtrate provided a pale yellow viscous oil which was crystallized from acetonitrile-ether. The resulting solid was collected by filtration, washed with cold acetonitrile-ether and dried 24 hours under vacuum at 90° C. to give 13.6 g. of 1,5-bis-[4-(2-ethylhexylamino)-1-pyridinium]pentane dibromide, m.p. 150°–151° C.

EXAMPLE 54

Following a procedure similar to that described in Example 53 but employing 12.4 g. (0.06 mole) of 4-(2-ethylhexylamino)pyridine and 7.32 g. (0.03 mole) of 1,6-dibromohexane there was obtained 16.1 g. of 1,6-bis-[4-(2-ethylhexylamino)-1-pyridinium]hexane dibromide, m.p. 208°–209° C.

EXAMPLE 55

Following a procedure similar to that described in Example 53 but employing 12.4 g. (0.06 mole) of 4-(2-ethylhexylamino)pyridine and 7.75 g. (0.03 mole) of 1,7-dibromoheptane there was obtained 17.9 g. of 1,7-bis-[4-(2-ethylhexylamino)-1-pyridinium]heptane dibromide, m.p. 219°–220° C.

EXAMPLE 56

Following a procedure similar to that described in Example 53 but employing 12.4 g. (0.06 mole) of 4-(2-ethylhexylamino)pyridine and 8.2 g. (0.03 mole) of 1,8-dibromooctane there was obtained 15.9 g. of 1,8-bis-[4-(2-ethylhexylamino)-1-pyridinium]octane dibromide, m.p. 160°–161° C.

EXAMPLE 57

Following a procedure similar to that described in Example 53 but employing 12.4 g. (0.06 mole) of 4-(2-ethylhexylamino)pyridine and 8.6 g. (0.03 mole) of 1,9-dibromononane there was obtained 15.2 g. of 1,9-bis-[4-(2-ethylhexylamino)-1-pyridinium]nonane dibromide, m.p. 158°–159° C.

EXAMPLE 58

Following a procedure similar to that described in Example 53 but employing 12.4 g. (0.06 mole) of 4-(2-ethylhexylamino)pyridine and 9.0 g. (0.03 mole) of 1,10-dibromodecane there was obtained 17.4 g. of 1,10-bis-[4-(2-ethylhexylamino)-1-pyridinium]decane dibromide, m.p. 162°–163° C.

EXAMPLE 59

Following a procedure similar to that described in Example 2 but employing 5.0 g. of 1,10-bis-[4-(2-ethylhexylamino)-1-pyridinium]decane dibromide there was obtained 4.11 g. of the corresponding dichloride, m.p. 191°–192° C.

EXAMPLE 60

To a stirred warm solution containing 12.0 g. (0.063 mole) of 4-(heptylamino)pyridine in 100 ml. of acetonitrile there was added dropwise a solution containing 7.4 g. (0.032 mole) of 1,5-dibromopentane in 25 ml. of acetonitrile and the resulting mixture heated 19 hours under reflux. The reaction mixture was cooled in ice and ether was gradually added until a colorless solid precipitated. The solid was collected by filtration recrystallized from acetonitrile-ether and dried 48 hours at 90° C./1 mm. to give 15.9 g. of 1,5-bis-[4-(heptylamino)-1-pyridinium]pentane dibromide, m.p. 153°–154° C.

EXAMPLE 61

Following a procedure similar to that described in Example 60 but using 19.2 g. (0.1 mole) of 4-(heptyl)-amino)pyridine and 12.2 g. (0.05 mole) of 1,6-dibromohexane there was obtained 27.5 g. of crude product. Recrystallization of a 15-gram sample from acetonitrile-ether afforded 11.45 g. of 1,6-bis-[4-(heptylamino)-1-pyridinium]hexane dibromide, m.p. 149°–150° C.

EXAMPLE 62

A. A suspension of 24.0 g. of crude 1,6-bis-[4-(heptylamino)-1-pyridinium]hexane dibromide in 500 ml. of water was made alkaline with 3 N aqueous sodium hydroxide and extracted with chloroform. The chloroform extracts were dried over anhydrous sodium sulfate and evaporated to dryness under reduced pressure. The residual oil was dissolved in methanol and the resulting solution acidified with methanesulfonic acid and evaporated to dryness under reduced pressure. The residue was redissolved in methanol, treated with decolorizing carbon, filtered and evaporated to dryness under vacuum leaving an oily residue which upon trituration with ether followed by acetonitrile provide 18.2 g. of gummy solid. The crude solid was dissolved in water and the resulting solution make alkaline with 35% aqueous sodium hydroxide and extracted with chloroform. The chloroform extracts were dried over anhydrous sodium sulfate and evaporated to dryness under reduced pressure. The resulting solid was triturated successively with ether and acetonitrile, collected by filtration and dried to give 16.3 g. of tan solid, m.p. 105°–108° C. The solid so-obtained was dissolved in 100 ml. of methanol and the resulting solution acidified with methanesulfonic acid. Evaporation to dryness under reduced pressure produced a viscous oil which was taken up in 20 ml. of methanol and treated portionwise with 150 ml. of water. The resulting suspension was cooled in ice and the suspended solid was collected by filtration and washed with cold water. The solid was then slurried in hot acetone, cooled, collected by filtration, washed with cold acetone and dried 48 hours at 95° C./1 mm. to give 10.8 g. of tan solid, m.p. 163°–165° C. This product gave a positive chloride ion test with silver nitrate and the nmr spectrum thereof indicated the absence of the methanesulfonate group.

B. A suspension of 14.0 g. of 1,6-bis-[4-(heptylamino)-1-pyridinium]hexane dibromide in 500 ml. of water was made allkaline with 35% aqueous sodium hydroxide and extracted with chloroform. The chloroform extracts were dried over anhydrous sodium sulfate and evaporated to dryness under reduced pressure. The partially solid residue was dissolved in 1 l. of acetonitrile-benzene and the resulting solution evaporated to dryness under vacuum. This process was repeated three times. The final residue was dissolved in 50 ml. of acetonitrile and the resulting solution diluted with 50 ml. of benzene and cooled in ice to give after filtering and drying 5.3 g. of tan solid. The filtrate afforded a second crop of 4.8 g. The crops were combined and dissolved in 50 ml. of acetonitrile. Dilution with ether precipitated a solid which was collected by filtration and dried 48 hours at 95° C./1 mm. to give 8.85 g. of tan solid, m.p. 174°–176° C. This product also gave a positive chloride ion test with silver nitrate.

C. The products of parts A and B above were combined, mixed with 300 ml. of water and heated until a homogeneous solution was obtained. The solution was filtered and the filtrate treated with 50 ml. of 12 N hydrochloric acid. The resulting suspension was concentrated under reduced pressure and the residue was treated with ice. The solid so-produced was collected by filtration, washed with cold water and dried. The product was then dissolved in acetone, the resulting solution diluted with a mixture of benzene and ethanol, and the whole evaporated to dryness under vacuum. The solid residue was slurried in 100 ml. of acetone and the slurry diluted with ether and filtered to give after drying 48 hours at 105° C./1 mm. and 72 hours at 115° C./1 mm. 16.3 g. of crude 1,6-bis-[4-(heptylamino)-1-pyridinium]hexane dichloride as an off-white solid, m.p. 176°–178° C.

EXAMPLE 63

Following a procedure similar to that described in Example 60 but employing 10.30 g. (0.050 mole) of 4-(2-ethylhexylamino)pyridine and 5.4 g. (0.025 mole) of 1,4-dibromobutane there was obtained 14.9 g. of 1,4-bis-[4-(2-ethylhexylamino)-1-pyridinium]butane dibromide, m.p. 245°–246° C.

EXAMPLE 64

A. A mixture containing 229 g. (1.0 mole) of N-(4-pyridyl)pyridinium chloride hydrochloride and 244 g. (1.26 moles) of n-decylamine hydrochloride was stirred and heated approximately 2.5 hours at 190°–195° C. The reaction mixture was then allowed to cool slowly to 40° C. and diluted with 2 l. of water. The resulting solution was cooled by the addition of ice and made alkaline with 200 ml. of 35% aqueous sodium hydroxide. The dark solid which separated was collected by filtration and washed with cold water. This material was dissolved in 1 l. of chloroform and the resulting solution was treated with decolorizing carbon and filtered. The filtrate was evaporated under reduced pressure and the residue was triturated with 150 ml. of ether. The solid thus-obtained was redissolved in chloroform and the resulting solution treated with decolorizing carbon and filtered. The filtrate was again treated with decolorizing carbon and filtered. The filtrate was evaporated to dryness under reduced pressure and the residual solid was triturated with ether. Recrystallization from acetonitrile afforded after drying under vacuum 96.1 g. of 4-(decylamino)pyridine, m.p. 71°–73° C.

B. To a stirred, warm solution containing 12.2 g. (0.052 mole) of 4-(decylamino)pyridine in 150–170 ml. of acetonitrile was added dropwise a solution containing 6.35 g. (0.026 mole) of 1,6-dibromohexane in 60 ml. of acetonitrile and the resulting mixture heated approximately 20 hours under reflux. The reaction mixture was then cooled in ice and the precipitated solid was collected by filtration and washed with cold acetonitrile. The product thus-obtained was dissolved in methanol and the resulting solution treated with decolorizing carbon and filtered. The filtrate was evaporated to dryness under reduced pressure and the residue was triturated with 50 ml. of cold ether, collected by filtration and dried 2 days over phosphorus pentoxide at 70° C./0.1 mm. to give 14.6 g. of 1,6-bis-[4-(decylamino)-1-pyridinium]hexane dibromide, m.p. 138°–140° C.

EXAMPLE 65

Following a procedure similar to that described in Example 64B but employing 12.2 g. (0.052 mole) of 4-(decylamino)pyridine and 6.7 g. (0.026 mole) of 1,7-dibromoheptane there were obtained 16.0 g. of 1,7-bis-[4-(decylamino)-1-pyridinium]heptane dibromide, m.p. 145°–147° C.

EXAMPLE 66

Following a procedure similar to that described in Example 64B but employing 11.7 g. (0.050 mole) of 4-(decylamino)pyridine and 6.8 g. (0.025 mole) of 1,8-dibromooctane there was obtained 16.9 g. of 1,8-bis-[4-(decylamino)-1-pyridinium]octane dibromide, m.p. 180°–182° C.

EXAMPLE 67

Following a procedure similar to that described in Example 64B but employing 11.7 g. (0.050 mole) of 4-(decylamino)pyridine and 7.15 g. (0.025 mole) of 1,9-dibromononane there was obtained 15.1 g. of 1,9-bis-[4-(decylamino)-1-pyridinium]nonane dibromide, m.p. 124°–126° C.

EXAMPLE 68

Following a procedure similar to that described in Example 64B but employing 11.2 g. (0.048 mole) of 4-(decylamino)pyridine and 7.2 g. (0.024 mole) of 1,10-dibromodecane there was obtained 14.6 g. of 1,10-bis-[4-(decylamino)-1-pyridinium]decane dibromide, m.p. 173°–174° C.

EXAMPLE 69

Following a procedure similar to that described in Example 64B but employing 11.2 g. (0.048 mole) of 4-(decylamino)pyridine and 7.9 g. (0.024 mole) of 1,12-dibromododecane there was obtained 16.5 g. of 1,12-bis-[4-(decylamino)-1-pyridinium]dodecane dibromide, m.p. 102°–106° C.

EXAMPLE 70

To a stirred warm solution containing 13.6 g. (0.052 mole) of 4-(decylamino)pyridine in 140 ml. of acetonitrile was added dropwise a solution containing 6.34 g. (0.026 mole) of 1,6-dibromohexane in 50 ml. of acetonitrile and the resulting mixture heated under reflux overnight. The reaction mixture was cooled and the precipitated solid was collected by filtration. The collected solid was dissolved in absolute ethanol and the resulting solution treated with decolorizing carbon and filtered. The filtrate was evaporated to dryness under reduced pressure affording a residual white solid which was slurried in ether, collected by filtration and dried at 60° C./0.1 mm. to give 17.63 g. of 1,6-bis-[4-(dodecylamino)-1-pyridinium]hexane dibromide, m.p. 164°–165° C.

EXAMPLE 71

Following a procedure similar to that described in Example 70 but employing 13.6 g. (0.052 mole) of 4-(dodecylamino)pyridine and 6.71 g. (0.026 mole) of 1,7-dibromoheptane there was obtained 18.03 g. of 1,7-bis-[4-(dodecylamino)-1-pyridinium]heptane dibromide, m.p. 148°–150° C.

EXAMPLE 72

Following a procedure similar to that described in Example 70 but employing 12.59 g. (0.048 mole) of 4-(dodecylamino)pyridine and 6.53 g. (0.024 mole) of 1,8-dibromooctane there was obtained 16.18 g. of 1,8-bis-[4-(dodecylamino)-1-pyridinium]octane dibromide, m.p. 184°–185° C.

EXAMPLE 73

Following a procedure similar to that described in Example 70 but employing 12.59 g. (0.048 mole) of 4-(dodecylamino)pyridine and 6.86 g. (0.024 mole) of 1,9-dibromononane there was obtained 19.35 g. of 1,9-bis-[4-(dodecylamino)-1-pyridinium]nonane dibromide, m.p. 134°–135° C.

EXAMPLE 74

Following a procedure similar to that described in Example 70 but employing 12.59 g. (0.048 mole) of 4-(dodecylamino)pyridine and 7.2 g. (0.024 mole) of 1,10-dibromodecane there was obtained 18.08 g. of 1,10-bis-[4-(dodecylamino)-1-pyridinium]decane dibromide, m.p. 178°–180° C.

EXAMPLE 75

Following a procedure similar to that described in Example 70 but employing 11.54 g. (0.044 mole) of 4-(dodecylamino)pyridine and 7.22 g. (0.022 mole) of 1,12-dibromododecane there was obtained 17.68 g. of 1,12-bis-[4-(dodecylamino)-1-pyridinium]dodecane dibromide, m.p. 75°–77° C.

EXAMPLE 76

A. To a stirred warm solution containing 21.0 g. (0.102 mole) of 4-(p-chlorophenylamino)pyridine in 150 ml. of N,N-dimethylformamide was added dropwise a solution containing 11.02 g. (0.051 mole) of 1,4-dibromobutane in 50 ml. of acetonitrile and the resulting mixture was heated 2.5 hours on a steam bath. The reaction mixture was cooled to room temperature, diluted with ether and the product allowed to crystallize. The precipitated solid was collected by filtration, washed with a mixture of acetonitrile and ether and air-dried to give 27.4 g. of 1,4-bis-[4-(p-chlorophenylamino)-1-pyridinium]butane dibromide, m.p. 182°–189° C.

B. A suspension of the above product in 500 ml. of water was treated with ice and 2 N aqueous sodium hydroxide and the resulting mixture extracted thoroughly with chloroform. The chloroform extracts were dried over anhydrous sodium sulfate and evaporated to dryness under reduced pressure to give 21.0 g. of the corresponding anhydro base as an oil which solidified on standing.

C. A solution containing the above anhydro base in 250 ml. of methanol was acidified with a solution of methane-sulfonic acid in methanol. Evaporation to dryness under reduced pressure afforded an oil which was crystallized from methanol-ether. The solid thus-obtained was recrystallized from methanol-ether to give after drying 48 hrs. at 92° C./0.1 mm. 18.95 g. of 1,4-bis-[4-(p-chlorophenylamino)-1-pyridinium]butane dimethanesulfonate, m.p. 245°–247° C.

EXAMPLE 77

A. To a stirred, warm solution containing 21.0 g. (0.102 mole) of 4-(p-chlorophenylamino)pyridine in 200 ml. of N,N-dimethylformamide was added dropwise a solution containing 12.45 g. (0.051 mole) of 1,6-dibromohexane in 50 ml. of acetonitrile and the resulting mixture was heated 4 hours on a steam bath. Upon cooling to room temperature a solid began to precipitate. The reaction mixture was diluted with 150 ml. of acetonitrile and cooled further in ice. The precipitated solid was collected by filtration and air-dried to give 27.2 g. of 1,6-bis-[4-(p-chlorophenylamino)-1-pyridinium]hexane dibromide, m.p. 148°–150° C.

B. A methanol solution of the corresponding anhydro base prepared from the above dibromide according to the procedure of Example 76B was acidified with methanesulfonic acid and then evaporated to dryness under reduced pressure. The residual oil was crystallized from acetone-methanol to give after drying 48 hrs. at 75° C./0.1 mm. 25.2 g. of 1,6-bis-[4-(p-chlorophenylamino)-1-pyridinium]hexane dimethanesulfonate, m.p. 108°–110° C.

EXAMPLE 78

A. To a stirred, warm solution containing 21.0 g. (0.102 mole) of 4-(p-chlorophenylamino)pyridine in 200 ml. of N,N-dimethylformamide was added dropwise a solution containing 13.9 g. (0.051 mole) of 1,8-dibromooctane in 50 ml. of acetonitrile and the resulting mixture heated 1.5 hours on a steam bath. The reaction mixture was then diluted with 100 ml. of acetonitrile and heating was continued another 2.5 hours when an additional 100 ml. of acetonitrile was added. After heating another 2 hours the reaction mixture was cooled and the solid which had precipitated was collected by filtration, washed with a mixture of acetonitrile and ether and dried to give 30.1 g. of 1,8-bis-[4-(p-chlorophenylamino)-1-pyridinium]octane dibromide, m.p. 245°–247° C.

B. A methanol solution of the corresponding anhydro base prepared from the above dibromide according to the procedure of Example 76B was acidified with methanesulfonic acid and then evaporated to dryness under reduced pressure. The residual oil was dissolved in acetonitrile and the resulting solution treated with acetone until cloudy followed by clarification with a small amount of methanol and cooled. The crude solid which precipitated was collected and recrystallized from acetonitrile acetone to give after drying 36 hours at 80° C./0.1 mm., 23.5 g. of 1,8-bis-[4-(p-chlorophenylamino)-1-pyridinium]octane dimethanesulfonate, m.p. 164°-165° C.

EXAMPLE 79

A. To a stirred, warm solution containing 21.0 g. (0.102 mole) of 4-(p-chlorophenylamino)pyridine in 200 ml. of N,N-dimethylformamide was added dropwise a solution containing 15.3 g. (0.051 mole) of 1,10-dibromodecane in 50 ml. of acetonitrile and the resulting mixture was heated 3.5 hours on a steam bath. The reaction mixture was then evaporated to dryness under reduced pressure and the residual oil was crystallized from methanol-acetonitrile. The solid so-produced was collected by filtration and washed with a cold mixture of acetonitrile and ether to give 28.0 g. of 1,10-bis-[4-(p-chlorophenylamino)-1-pyridinium]decane dibromide, m.p. 225°-230° C.

B. A methanol solution of the corresponding anhydro base prepared from the above dibromide according to the procedure of Example 76B was acidified with methanesulfonic acid and then evaporated to dryness under reduced pressure. The residual oil was crystallized from acetonitrile-ether. The crude solid thus-obtained was dissolved in methanol and the resulting solution was treated with decolorizing carbon and filtered. Evaporation of the filtrate afforded an oil which was suspended in a mixture of acetonitrile and acetone to give a crude solid. Recrystallization from methanol-ether afforded after drying 48 hours at 95° C./0.1 mm. 18.4 g. of 1,10-bis-[4-(p-chlorophenylamino)-1-pyridinium]decane dimethanesulfonate, m.p. 202°-204° C.

EXAMPLE 80

To a stirred warm solution containing 10.0 g. (0.049 mole) of 4-(p-chlorophenylamino)pyridine in a mixture of 275 ml. of acetonitrile and 100 ml. of N,N-dimethylformamide was added dropwise a solution containing 5.75 g. (0.025 mole) of 1,5-dibromopentane in 25 ml. of acetonitrile and the resulting mixture heated 24 hours under reflux. The reaction mixture was then evaporated to dryness under reduced pressure and the residue triturated with a mixture of ether and acetonitrile. The pale yellow solid so-obtained was redissolved in ethanol and the resulting solution treated with decolorizing carbon and filtered. The filtrate was evaporated to dryness under reduced pressure and the residual oil was crystallized from ether-acetonitrile. The colorless solid was recrystallized from methanolacetonitrile and dried 48 hours at 115° C./0.1 mm. to give 8.1 g. of 1,5-bis-[4-(p-chlorophenylamino)-1-pyridinium]pentane dibromide, m.p. 166°-168° C.

EXAMPLE 81

To a stirred, warm solution containing 10.0 g. (0.049 mole) of 4-(p-chlorophenylamino)pyridine in a mixture of 125 ml. of N,N-dimethylformamide and 50 ml. of acetonitrile was added dropwise a solution containing 6.45 g. of 1,7-dibromoheptane in 25 ml. of acetonitrile and the resulting mixture heated 19 hours under reflux. The reaction mixture was then evaporated to dryness under reduced pressure and the residual oil crystallized from ethanol-acetonitrile. The solid so-produced was dissolved in methanol and the resulting solution treated with decolorizing carbon and filtered. The filtrate was evaporated to dryness under vacuum and the residual oil again crystallized from ethanol-acetonitrile. The product was collected by filtration and dried 36 hours at 105° C./0.1 mm. to give 10.4 g. of 1,7-bis-[4-(p-chlorophenylamino)-1-pyridinium]heptane dibromide, m.p. 202°-204° C.

EXAMPLE 82

Following a procedure similar to that described in Example 81 but employing 10.0 g. (0.049 mole) of 4-(p-chlorophenylamino)pyridine and 7.15 g. (0.025 mole) of 1,9-dibromononane there was obtained 11.2 g. of 1,9-bis-[4-(p-chlorophenylamino)-1-pyridinium]nonane dibromide, m.p. 178°-179° C.

EXAMPLE 83

A. A mixture containing 64.0 g. (0.43 mole) of p-fluoroaniline hydrochloride and 4-chloropyridine hydrochloride was heated gradually to an internal temperature of 170° C. whereupon the solid mixture began to melt and stirring was begun. Upon continued heating, the melt began to resolidify. Stirring was stopped and heating was continued until no further change was evident. The mixture was cooled, dissolved in 1 liter of water and ice, and the solution made alkaline with 35% sodium hydroxide. The resulting precipitate was collected, washed with water and redissolved in hot methanol. The methanol solution was treated with decolorizing carbon, filtered and evaporated to dryness. The residue was recrystallized twice from chloroform-acetonitrile-ether to give after drying 47.3 g. of 4-(p-fluorophenylamino)pyridine, m.p. 195°-198° C.

B. To a warm, stirred solution containing 7.5 g. (0.04 mole) of 4-(p-fluorophenylamino)pyridine in a mixture of 75 ml. of acetonitrile and 25 ml. of N,N-dimethylformamide was added dropwise over 0.25 hour 4.9 g. (0.020 mole) of 1,6-dibromohexane. The resulting mixture was heated 18 hours under gentle reflux, and then cooled to 0° C. The solution was seeded with crystals of the desired product (previously obtained by diluting a small aliquot of the reaction mixture with ether) and the resulting precipitate was collected and washed with cold ether. The solid was dissolved in methanol and the resulting solution was treated with decolorizing carbon, filtered and evaporated to dryness. The residue was recrystallized from methanol-acetonitrile-ether to give 9.3 g. of 1,6-bis-[4-(p-fluorophenylamino)-1-pyridinium]hexane dibromide, m.p. 220°-222° C.

EXAMPLE 84

Following a procedure similar to that described in Example 83B but employing 7.5 g. (0.04 mole) of 4-(p-fluorophenylamino)pyridine and 5.4 g. (0.020 mole) of 1,8-dibromooctane there was obtained 8.65 g. of 1,8-bis-[4-p-fluorophenylamino)-1-pyridinium]octane dibromide, m.p. 226°-228° C.

By following procedures similar to those described in the foregoing examples, the following bis-[4-(R-amino)-1-pyridinium]alkanes are obtained:

3-ethyl-1,6-bis-[4-(tetradecylamino)-1-pyridinium]-hexane dibromide by reacting 1,6-dibromo-3-ethylhexane with 4-(tetradecylamino)pyridine which is in turn obtained by reacting N-(4-pyridyl)pyridinium chloride hydrochloride with tetradecylamine hydrochloride, 1,5-bis-[4-(octadecylamino)-1-pyridinium]pentane dibromide by reacting 1,5-dibromopentane with 4-(octadecylamino)pyridine which in turn is obtained by reacting N-(4-pyridyl)pyridinium chloride hydrochloride with octadecylamine hydrochloride, 1,11-bis-[4-(2,2-dimethylbutylamino)-1-pyridinium]-3-methylundecane dibromide by reacting 1,11-dibromo-3-methyl-undecane with 4-(2,2-dimethylbutylamino)pyridine which in turn is obtained by reacting N-(4-pyridyl)pyridinium chloride hydrochloride with 2,2-dimethylbutylamine hydrochloride, 1,18-bis-[4-(1,4-dimethylpentylamino)-1-pyridinium]-octadecane dibromide by reacting 1,18-dibromooctadecane with 4-(1,4-dimethylpentylamino)pyridine which in turn is obtained by reacting N-(4-pyridyl)pyridinium chloride hydrochloride with 1,4-dimethylpentylamine hydrochloride, 4,9-dimethyl-1,12-bis-[4-(1,5-dimethyl-4-ethyl-hexylamino)-1-pyridinium]dodecane dibromide by reacting 1,12-dibromo-4,9-dimethyldodecane with 4-(1,5-dimethyl-4-ethylhexylamino)pyridine which in turn is obtained by reacting N-(4-pyridyl)pyridinium chloride hydrochloride with 1,5-dimethyl-4-ethylhexylamine hydrochloride, 1,10-bis-[4-(cyclopentylamino)-1-pyridinium]-decane dichloride by reacting 1,10-dichlorodecane with 4-(cyclopentylamino)pyridine which in turn is obtained by reacting N-(4-pyridyl)pyridinium chloride hydrochloride with cyclopentylamine hydrochloride, 1,12-bis-[4-(cycloheptylamino)-1-pyridinium]-dodecane dibromide by reacting 1,12-dibromododecane with 4-(cycloheptylamino)pyridine which in turn is obtained by reacting N-(4-pyridyl)pyridinium chloride hydrochloride with cycloheptylamine hydrochloride, 1,6-bis-[4-(p-bromophenylamino)-1-pyridinium]-3-methylhexane dibromide by reacting 1,6-dibromo-3-methylhexane with 4-(p-bromophenylamino)pyridine which in turn is obtained by reacting N-(4-pyridyl)-pyridinium chloride hydrochloride with p-bromoaniline hydrochloride, 1,10-bis-[4-(m-fluorophenylamino)-1-pyridinium]-decane dibromide by reacting 1,10-dibromodecane with 4-(m-fluorophenylamino)pyridine which in turn is obtained by reacting N-(4-pyridyl)pyridinium chloride hydrochloride with m-fluoroaniline hydrochloride, 1,4-bis-[4-(3-chloro-4-fluorophenylamino)-1-pyridinium]-2-ethylbutane dibromide by reacting 1,4-dibromo-2-ethylbutane with 4-(3-chloro-4-fluorophenylamino)-pyridine which in turn is obtained by reacting N-(4-pyridyl)pyridinium chloride hydrochloride with 3-chloro-4-fluoroaniline hydrochloride, 1,10-bis-[4-(benzylamino)-1-pyridinium]decane dichloride by reacting 1,10-dichlorodecane with 4-(benzylamino)pyridine, 1,8-bis-[4-(3,4-methylenedioxyphenylamino)-1-pyridinium]octane dibromide by reacting 1,8-dibromooctane with 4-(3,4-methylenedioxyphenylamino)pyridine which in turn is obtained by reacting N-(4-pyridyl)pyridinium chloride hydrochloride with 3,4-methylenedioxyaniline hydrochloride, 1,9-bis-[4-(p-ethylphenylamino)-1-pyridinium]nonane dibromide by reacting 1,9-dibromononane with 4-(p-ethylphenylamino)pyridine which in turn is obtained by reacting N-(4-pyridyl)pyridinium chloride hydrochloride with p-ethylaniline hydrochloride, 1,10-bis-[4-(p-methoxyphenylamino)-1-pyridinium]-decane dichloride by reacting 1,10-dichlorodecane with 4-(p-methoxyphenylamino)pyridine which is in turn obtained by reacting N-(4-pyridyl)pyridinium chloride hydrochloride with p-anisidine hydrochloride, 1,11-bis-[4-(m-nitrophenylamino)-1-pyridinium]-undecane dibromide by reacting 1,11-dibromoundecane with 4-(m-nitrophenylamino)pyridine which in turn is obtained by reacting N-(4-pyridyl)pyridinium chloride hydrochloride with m-nitroaniline hydrochloride, 1,12-bis-[4-(o-cyanophenylamino)-1-pyridinium]-dodecane dibromide by reacting 1,12-dibromododecane with 4-(o-cyanophenylamino)pyridine which in turn is obtained by reacting N-(4-pyridyl)pyridinium chloride hydrochloride with o-cyanoaniline hydrochloride, 1,16-bis-<4-[m-(trifluoromethyl)phenylamino]-1-pyridinium>hexadecane dibromide by reacting 1,16-dibromohexadecane and 4-[m-(trifluoromethyl)-phenylamino]pyridine which in turn is obtained by reacting N-(4-pyridyl)pyridinium chloride hydrochloride with m-(trifluoromethyl)aniline hydrochloride, 1,7-bis-[4-(2-methoxy-5-methylphenylamino)-1-pyridinium]heptane dibromide by reacting 1,7-dibromoheptane with 4-(2-methoxy-5-methylphenylamino)pyridine which in turn is obtained by reacting N-(4-pyridyl)pyridinium chloride hydrochloride with 2-methoxy-5-methylaniline hydrochloride, 1,10-bis-[2-methyl-4-(octylamino)-1-pyridinium]-decane dibromide by reacting 1,10-dibromodecane with 2-methyl-4-(octylamino)pyridine which is in turn obtained by reacting 4-chloro-2-methylpyridine hydrochloride with n-octylamine hydrochloride, 1,8-bis-[3-ethyl-4-(heptylamino)-1-pyridinium]-octane dibromide by reacting 1,8-dibromooctane with 3-ethyl-4-(heptylamino)pyridine which is in turn obtained by reacting 4-chloro-3-ethylpyridine hydrochloride with n-heptylamine hydrochloride, 1,10-bis-[4-(octylamino)-1-pyridinium]-1-methyldecane dibromide by reacting 1,10-dibromo-1-methyldecane with 4-(octylamino)pyridine.

The following are further illustrative examples of bis-[4-(R-amino)-1-pyridinium]alkanes of Formula I which are obtained in accordance with the above-described procedures:

3-methyl-1,5-bis-[4-(undecylamino)-1-pyridinium]-pentane dibromide, 3-propyl-1,5-bis-[4-(tridecylamino)-1-pyridinium]pentane dichloride, 4,4-dimethyl-1,7-bis-[4-(pentadecylamino)-1-pyridinium]heptane sulfate, 2,6-dimethyl-1,7-bis-[4-(hexadecylamino)-1-pyridinium]-heptane disulfamate, 1-methyl-1,4-bis-[4-(heptadecylamino)-1-pyridinium]butane dibenzenesulfonate, 2,4,4-trimethyl-1,6-bis-[4-(2-methylhexylamino)-1-pyridinium]hexane bis-cyclohexylsulfamate, 1,17-bis-[4-(3-ethylpentylamino)-1-pyridinium]-heptadecane dibromide, 1,16-bis-[4-(1-ethylhexylamino)-1-pyridinium]-hexadecane dinitrate, 1,15-bis-[4-(heptylamino)-1-pyridinium]pentadecane dibromide, 1,13-bis-[4-(octylamino)-1-pyridinium]tridecane di-2-naphthalenesulfonate, 1,11-bis-[4-(3-ethylheptylamino)-1-pyridinium-]undecane 2,6-naphthalenedisulfonate,-4-methyl-1,14-bis-[4-(2-propylpentylamino)-1-pyridinium]tetradecane dichloride, 5-ethyl-1,9-bis[4-(1,3,5-trimethylhexylamino)-1-pyridinium]nonane dibromide, 3,3,6,6,-tetramethyl-1,8-bis-[4-(heptylamino)-1-pyridinium]-octane dibromide, 2,13-dimethyl-1,14-bis-[4-(1,2-dimethyl-tetradecylamino)-1-pyridinium]tetradecyl dibromide, 1,6-bis[4-(1-methylpentylamino)-1-pyridinium]hexane di-p-toluenesulfonate, 1,8-bis-[4-(2-methylheptylamino)-1-pyridinium]octane diiodide, 1,8-bis-[4-(2-methyl-3-ethylpentylamino)-1-pyridinium]octane diethanesulfonate, 1,9-bis-[4-(o-chlorophenylamino)-1-pyridinium]nonane dibromide, 1,8-bis-[4-(p-iodophenylamino)-1-pyridinium]octane diiodide, 1,12-bis-[4-(2,4-difluorophenylamino)-1-pyridinium]dodecane dibromide, 1,11-bis-[4-(2,5-dibromophenylamino)-1-pyridinium]undecane dibromide, 1,10-bis-[4-(3,5-dichlorophenylamino)-1-pyridinium]-decane dichloride, 1,8-bis-[4-(2-fluorobenzylamino)-1-pyridinium]octane dichloride, 1,18-bis-[4-(3,4-dichlorobenzylamino)-1-pyridinium]octadecane dibromide, 1,4-bis-[4-(4-hydroxy-3-methoxybenzylamino)-1-pyridinium]butane dibromide, 1,12-bis-[4-(4-methylbenzylamino)-1-pyridinium]dodecane dibromide, 1,12-bis-[3-isopropyl-4-(hexylamino)-1-pyridinium]dodecane dichloride, 1,9-bis-[2-n-butyl-4-(nonylamino)-1-pyridinium]nonane dibromide, 1,12-bis-[4-(2-ethylhexylamino)-2-methyl-1-pyridinium]dodecane dibromide, 1,8-bis-[4-(cyclohexylamino)-2-methyl-1-pyridinium]octane dibromide and 1,9-bis-[4-(p-chlorophenylamino)-2-methyl-1-pyridinium]nonane dibromide.

As indicated hereinabove and exemplified in Table A hereinbelow, the novel compounds of Formula I have useful antibacterial and antifungal activity being effective against both gram positive and gram negative bacteria, and several species of fungi. Of particular importance is the fact that the compounds are highly active against *Pseudomonas aeruginosa* and *Proteus mirabilis*, two ubiquitous gram negative bacteria which are often the pathogens associated with hospital-acquired infections and which are often resistant to other currently used antibacterial agents. Thus the present compounds are true broad spectrum antibacterial agents. Moreover, these compounds are virucidally effective against Herpes viruses.

By comparison, the most closely related prior art compounds (compounds I-IX in Table A), i.e.
I. 1,8-bis-(4-amino-1-pyridinium)octane dibromide,
II. 1,10-bis-(4-amino-1-pyridinium)decane dibromide,
III. 1,4-bis-(4-amino-1-pyridinium)butane dibromide,
IV. 1,6-bis-(4-amino-1-pyridinium)hexane dibromide,
V. 1,12-bis-(4-amino-1-pyridinium)dodecane dibromide,
VI. 1,10-bis-(4-amino-1-pyridinium)-1-methyldecane dibromide,
VII. 1,9-bis-(4-amino-1-pyridinium)nonane dibromide,
VIII. 1,8-bis-(4-amino-2-methyl-1-pyridinium)octane dibromide, and
IX. 1,9-bis-(4-amino-2-methyl-1-pyridinium)nonane dibromide,
are relatively weakly active, have a narrow spectrum of activity and are essentially inactive against both *Pseudomonas aeruginosa* and *Proteus mirabilis*. Nevertheless, the discovery of this relatively weak and specific antimicrobial activity is considered a part of the present invention and accordingly the method of using the known compounds as antimicrobial agents is claimed herein. However, it is clear that the novel claimed compounds of Formula I possess marked advantages over the known compounds both in terms of potency and spectrum of activity and are accordingly believed unobvious over and patentably distinct from the known compounds.

The antibacterial and antifungal activity of representative examples of the compounds of Formula I was determined using a modification of the Autotiter method described by Goss, et al. Applied Microbiology 16 (9) 1,414–1,416 (1968) in which a 1,000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from the cup by a Microtiter transfer loop and diluted in 0.05 ml. of sterile water. Following this operation, 0.05 ml. of inoculated double-strength semi-synthetic medium (glucose) is added automatically to each cup. The overall operation results in final drug concentrations ranging from 500 to 0.06 mcg./ml. in twofold decrements. The Autotray is incubated for 18–20 hours at 37° C. at which time the trays are examined visually for growth as evidenced by turbidity, and the concentration of the last sample in the series showing no growth (or no turbidity) is recorded as the minimal inhibitory concentration (MIC) in mcg./ml. The compounds were thus tested as solutions against a variety of gram positive and gram negative bacteria including *Staphylococcus aureus*, *Proteus mirabilis*, *Escherichia coli*, *Klebsiella pneumoniae*, *Pseudomonas aeruginosa*, *Streptococcus pyogenes*, and against such fungi as *Aspergillus niger*, *Candida albicans* and *Trichophyton mentagrophytes*.

Many of the compounds of Formula I were also found to be antibacterially effective against *Streptococcus mutans* and *Actinomyces A-viscosis*.

The dental plaque preventive activity of certain of the compounds of the present invention was determined by measuring the ability of these compounds to inhibit the production of dental plaque by *Streptococcus mutans* OMZ-61 as follows:

A culture medium for the plaque-producing *Streptococcus mutans* OMZ-61 containing 1.5 g. of BBL beef extract, 5 g. of sodium chloride, 10 g. of dehydrated trypticase, 5 g. of sucrose and sufficient distilled water to give a total volume of 1000 ml. is adjusted to pH 7.0 and sterilized by membrane filtration. The medium is dispensed aseptically in 10-ml. aliquots into 150×16 mm. test tubes and stored at refrigeration temperature until used.

Two concentrations of the compound to be tested are prepared by dissolving 100 mg. of the compound in 1 ml. of distilled water with the aid of sufficient 0.1 N sodium hydroxide, 10% dimethylsulfoxide or 10% N,N-dimethylformamide and diluting the resulting solution to 10 ml. with distilled water. This 1.0% solution and a 1:10 dilution in distilled water (0.1%) are sterilized by membrane filtration before use.

A sterile piece of plaque-free natural tooth enamel or synthetic hydroxylapatite is suspended in each concentration of compound for two 1-minute periods, each followed by a 1-minute air drying period. Each piece is then suspended and agitated for 5 minutes in individual test tubes containing sterile distilled water (rinse). They are then suspended in 10 ml. of liquid beef extract medium to which has been added 0.3 ml. of a 24-hr. anaerobic culture of *Streptococcus mutans*. The tubes containing the "treated" hydroxylapatite and the *Streptococcus mutans* are then incubated anaerobically at 37° C. for 24 hours. The same process of two 1-minute soaks in the solution of compound, each followed by 1 minute of air drying and the final 5-minute rinse is repeated before once again suspending the hydroxylapatite in a fresh tube containing 10 ml. of beef extract medium and 0.3 ml. of inoculum. At the end of the second 24-hour period, each piece of hydroxylapatite is rinsed for 1 minute in 3 successive tubes of distilled water. These are then suspended for 1 minute in a solution of F, D & C Red No. 3 dye. This staining procedure is used in order to identify more easily the development of plaque after the 48-hour period of exposure to the plaque-producing organism. The staining period is followed by another 10-second rinse to remove excess dye. Any plaque formation stains a brilliant pink. Test results are read as plaque inhibition (active) or no plaque inhibition (inactive) at the percent concentration tested. Active compounds are tested at successively lower doses in order to determine the minimum effective concentration. On some occasions, the interference of plaque production is caused by the inhibition of growth of the organism in the culture medium because the compound has been leached from the hydroxylapatite to produce an antibacterial level in the medium. When this occurs, the compound is tested at lower concentrations until the growth of the organism in the surrounding medium is equal to that in the nonmedicated control culture. Plaque may or may not be formed at these lower concentrations.

Substantivity of the test compound to the tooth surface which is of course necessary to prevent the formation of dental plaque thereon, may, however, potentiate the accumulation of staining agents, e.g., coffee, tobacco, food colorants, etc., on the tooth surface. Therefore the above procedure was also utilized to estimate staining potential, i.e., the ability of the test compound to promote adherence of staining agents to the tooth surface. Thus, a residual, uniform pale pink color adhering to the test surface following the final rinse is indicative of staining potential at the precent concentration tested and is reported as staining concentration. The uniform pale pink color caused by the test compound is readily distinguished from the localized, brilliant pink color caused by plaque formation. In general the preferred species advantageously have a staining concentration considerably higher than the minimum effective plaque-preventive concentration.

Numerical antibacterial, antifungal, and dental plaque-preventive test data for the compounds are presented in Table A hereinbelow. Corresponding data for the above-identified known compounds I-IX are also included in Table A for purposes of comparison. Staining concentrations for representative examples are reported in Table C hereinbelow.

Antibacterial effectiveness in the presence of serum was determined for representative examples by the standard serial tube dilution test wherein paired comparisons of minimum inhibitory concentrations (MIC) were determined in the absence and in the presence of heat inactivated (30 min. at 56° C.) horse serum (40%) in the test medium. The results are expressed as the fold increase in MIC (mcg./ml.) versus *Staphyloccocus aureus* and *Escherichia coli* caused by the presence of serum and are presented in Table B hereinbelow.

Dental plaque-preventive effectiveness in the presence of sterile human saliva (50%) was determined for representative examples. Test results are read as minimum effective concentration and are presented in Table C hereinbelow.

Virucidal activity of representative examples against Herpes simplex type 2 virus was determined in vitro employing a procedure similar to the plaque inhibition test for detection of specific inhibitors of DNA-containing viruses published by E. C. Herrmann, Jr., Proc. Soc. Exp. Biol. Med. 107, 142 (1961) wherein 2 mg. of the test compound was placed on the surface of the growth medium. The compounds corresponding to Examples 1D, 3, 5C, 7, 9D, 11, 13, 17, 18, 21, 22, 24, 31, 33, 35, 36, 37, 53, 54, 55, 56, 57, 58, 60, 61, 63, 81 and 82 were found active and the compounds of Examples 16, 34, 39, 40 and 79B were found inactive.

The acute oral toxicity (ALD$_{50}$) of several representative examples was determined as follows: Groups of 3 young adult male Swiss-Webster strain albino mice were fasted approximately 4 hours before medication and then medicated once orally by stomach tube. All mice were observed for 7 days after medication. Autopsy of all mice in the study revealed no gross tissue changes except for the group receiving 1000 mg./kg. of the compound of Example 25 wherein congestion of the glandular portion of the stomachs of two of the three mice was observed. The results are presented in Table D hereinbelow.

TABLE A

In Vitro Antibacterial and Antifungal Activity MIC (mcg/ml)

| Cpd. of Ex. No. | S. Aureus Smith | E. coli Vogel | K. pneum. 39645 | P. mirab. MGH-1 | Ps. aerug. MGH-2 | E. coli AB1932-1 | E. coli 100/B22 | S. pyogen. C203 | A. niger 16404 | C. albicans 10231 | C. albicans Wisc. | T. menta. 9129 | Plaque Preventive Activity Concentration Tested (%) Active | Plaque Preventive Activity Concentration Tested (%) Inactive |
|---|---|---|---|---|---|---|---|---|---|---|---|---|---|---|
| 76C | 7.8 | 15.6 | >250 | >250 | >125 | 7.8 | 15.6 | 1.95 | >250 | 125 | 12.5 | 62.5 | | 1.0 |
| 77B | 3.9 | 15.6 | 500 | 500 | 500 | 3.9 | 15.6 | 1.95 | 62.5 | 62.5 | 125 | 15.6 | | 1.0 |
| 78B | 0.4 | 3.1 | 31.3 | 125 | 125 | 1.6 | 3.1 | 0.2 | 31.3 | 62.5 | 62.5 | 31.3 | | 1.0 |
| 79B | 0.4 | 1.6 | 3.1 | >125 | 62.5 | 0.8 | 1.6 | 0.4 | 25 | 3.13 | 6.25 | 6.25 | | 1.0 |
| 61 | 0.2 | 3.1 | 6.3 | >250 | 125 | 1.6 | 1.6 | 0.4 | 25 | 6.25 | 6.25 | 3.13 | | 1.0 |
| 62C | 0.24 | 3.9 | 3.9 | >125 | >62.5 | 1.95 | 1.95 | 0.98 | 7.8 | 3.9 | 3.9 | 3.9 | | 1.0 |
| 21 | 0.24 | 1.95 | 3.9 | 125 | 125 | 1.95 | 1.95 | 0.98 | 15.6 | 3.9 | 3.9 | 3.9 | 1.0 | |
| 60 | 0.49 | 31.3 | 31.3 | >125 | 125 | 3.9 | 7.8 | 1.95 | 15.6 | 15.6 | 15.6 | 7.8 | | 1.0 |
| 22 | 0.39 | 1.95 | 1.95 | 62.5 | 313 | 0.98 | 0.98 | 0.49 | 15.6 | 0.98 | 1.95 | 1.95 | 0.1 | |
| 17 | 0.49 | 31.3 | 125 | >250 | >125 | 7.8 | 7.8 | >78 | 250 | 7.8 | 15.6 | | 1.0 | |
| 18 | 0.39 | 15.6 | 15.6 | >125 | >125 | 7.8 | 7.8 | 0.49 | 15.6 | 6.25 | 7.8 | 15.6 | | 1.0 |
| 23 | 0.5 | 1.95 | 1.95 | 62.6 | 31.3 | 1.0 | 1.95 | 1.0 | 7.8 | 1.0 | 1.95 | 1.95 | 0.1 | |
| 32 | 0.24 | 3.9 | 7.8 | >250 | 125 | 1.95 | 3.9 | 0.49 | 7.8 | 3.9 | 3.9 | 7.8 | | 1.0 |
| 19 | 0.39 | 1.95 | 3.9 | 125 | 125 | 1.95 | 1.95 | 0.49 | 15.6 | 1.95 | 3.9 | 3.9 | | 1.0 |
| 33 | 0.195 | 1.95 | 3.9 | 31.3 | 31.3 | 0.98 | 1.95 | 0.49 | 3.9 | 1.95 | 3.9 | 1.95 | | 1.0 |
| 31 | 1.95 | 125 | >125 | >250 | >125 | 31.3 | 62.5 | 0.98 | 31.3 | 31.3 | 62.5 | 31.3 | | 1.0 |
| 16 | 7.8 | 125 | >125 | >125 | >250 | 62.5 | 125 | 1.95 | 125 | 125 | 125 | 15.6 | | 1.0 |
| 20 | 0.98 | 31.3 | >125 | >250 | >250 | 7.8 | 15.6 | 0.49 | 15.6 | 15.6 | 15.6 | 3.9 | | 1.0 |
| 26 | 0.37 | 0.75 | 1.49 | 6.0 | 11.9 | 0.75 | 0.75 | 1.95 | 2.98 | 0.75 | 1.49 | 0.75 | 0.01 | |
| 24 | 0.25 | 1.0 | 1.95 | 15.6 | 62.5 | 1.0 | 1.95 | 0.5 | 3.9 | 1.0 | 1.0 | 0.5 | 0.003 | |

TABLE A-continued

In Vitro Antibacterial and Antifungal Activity
MIC (mcg/ml)

| Cpd. of Ex. No. | S. Aureus Smith | E. coli Vogel | K. pneum. 39645 | P. mirab. MGH-1 | Ps. aerug. MGH-2 | E. coli AB1932-1 | E. coli 100/B22 | S. pyogen. C203 | A. niger 16404 | C. albicans 10231 | C. albicans Wisc. | T. menta. 9129 | Plague Preventive Activity Concentration Tested (%) Active | Inactive |
|---|---|---|---|---|---|---|---|---|---|---|---|---|---|---|
| 25 | 0.25 | 1.0 | 1.95 | 31.3 | 31.3 | 1.0 | 0.5 | 1.95 | 1.0 | 1.0 | 1.0 | 0.004 | | |
| 63 | 0.98 | 62.5 | >125 | >125 | 125 | 7.8 | 31.3 | 1.25 | 31.3 | 31.3 | 31.3 | 15.6 | | 1.0 |
| 53 | 0.49 | 15.6 | >125 | >125 | 125 | 7.8 | 15.6 | 0.625 | 31.3 | 31.3 | 15.6 | 7.8 | | 1.0 |
| 54 | 0.49 | 7.8 | 125 | >125 | >250 | 1.95 | 3.9 | 0.625 | 15.6 | 7.8 | 7.8 | 1.95 | | 1.0 |
| 55 | 0.49 | 3.9 | 7.8 | >125 | 125 | 3.9 | 3.9 | 0.49 | 15.6 | 7.8 | 7.8 | 1.95 | | 1.0 |
| 57 | 0.31 | 0.98 | 7.8 | 125 | 125 | 0.98 | 0.98 | 0.625 | 15.6 | 3.9 | 3.9 | 0.98 | | 1.0 |
| 27 | 0.25 | 0.5 | 1.0 | 7.8 | 7.8 | 1.0 | 0.5 | 0.5 | 3.9 | 1.96 | 1.0 | 1.0 | 0.004 | |
| 58 | 0.24 | 1.5 | 3.0 | 12.1 | 48.4 | 0.37 | 0.76 | 1.95 | 6.0 | 3.0 | 1.5 | 0.76 | 0.003 | |
| 59 | 0.25 | 1.0 | 1.95 | 7.8 | 31.3 | 1.0 | 0.5 | 1.0 | 15.6 | 1.95 | 1.95 | 1.0 | 0.003 | |
| 56 | 0.31 | 3.9 | 7.8 | 125 | 125 | 0.98 | 1.95 | 0.16 | 15.6 | 3.9 | 3.9 | 1.95 | 0.004 | |
| 81 | 0.98 | 3.9 | >125 | >125 | >125 | 125 | 3.9 | 0.49 | 31.3 | 31.3 | 31.3 | 7.8 | | 1.0 |
| 82 | 0.625 | 0.98 | 7.8 | >125 | 125 | 0.98 | 1.95 | 0.24 | 15.6 | 3.9 | 3.9 | 3.9 | | 1.0 |
| 34 | 125 | 125 | >500 | >500 | >500 | 125 | 125 | 31.3 | 500 | 500 | 500 | 125 | | 1.0 |
| 35 | 125 | >500 | >500 | >500 | >500 | >500 | >500 | 15.6 | 500 | 500 | 500 | 125 | | 1.0 |
| 36 | 15.6 | >125 | >125 | >125 | >125 | 125 | >125 | 15.6 | 125 | 125 | 125 | 15.6 | | 1.0 |
| 37 | 7.8 | >125 | >125 | >125 | 125 | 125 | >125 | 7.8 | >125 | 125 | 125 | 15.6 | | 1.0 |
| 80 | 7.8 | 125 | >125 | >125 | >125 | 31.3 | 125 | 1.95 | 62.5 | 62.5 | 62.5 | 15.6 | | 1.0 |
| 38 | 3.9 | 62.5 | >125 | >125 | 250 | 31.3 | 62.5 | 0.93 | 15.6 | 31.3 | 31.3 | 3.9 | | 1.0 |
| 40 | 0.24 | 15.6 | >125 | >125 | >125 | 7.8 | 15.6 | 3.9 | 7.8 | 3.9 | 7.8 | 1.95 | | 1.0 |
| 39 | 0.98 | 31.3 | 125 | >500 | 500 | 31.3 | 31.3 | 3.9 | 7.8 | 15.6 | 15.6 | 3.9 | | 1.0 |
| 3 | 0.39 | 1.56 | 3.13 | 3.13 | 6.25 | 6.25 | 3.13 | 0.39 | 3.13 | 1.56 | 3.13 | 1.56 | 0.004 | |
| 2 | 1.0 | 1.95 | 3.9 | 3.9 | 1.95 | 1.0 | 1.0 | 1.0 | 7.8 | 3.9 | 7.8 | 1.0 | 0.01 | |
| 4 | 0.25 | 0.5 | 1.95 | 1.95 | 3.9 | 1.0 | 0.5 | 1.0 | 7.8 | 1.95 | 1.95 | 0.5 | 0.003 | |
| 8 | 0.25 | 1.0 | 1.0 | 7.8 | 15.6 | 1.0 | 0.5 | 1.0 | 7.8 | 1.0 | 1.0 | 1.0 | 0.01 | |
| 1D | 0.77 | 1.54 | 0.77 | 1.54 | 3.0 | 3.0 | 0.77 | 1.95 | 3.0 | 1.54 | 1.54 | 0.77 | 0.1 | |
| 10A,B | 0.5 | 1.95 | 1.95 | 3.9 | 3.9 | 1.0 | 1.0 | 1.0 | 7.8 | 1.95 | 1.95 | 1.95 | 0.005 | |
| 7 | 0.15 | 0.37 | 1.5 | 6.0 | 23.8 | 0.37 | 0.37 | 1.0 | 3.0 | 0.74 | 0.74 | 0.37 | 0.01 | |
| 5C | 0.38 | 0.76 | 0.76 | 1.5 | 6.0 | 0.76 | 0.76 | 1.0 | 3.0 | 1.5 | 0.76 | 0.76 | 0.005 | |
| 6 | 0.5 | 1.0 | 1.0 | 3.9 | 3.9 | 0.5 | 0.5 | 1.95 | 3.9 | 1.0 | 1.95 | 0.5 | 0.004 | |
| 13 | 0.5 | 1.95 | 3.9 | 31.3 | 31.3 | 1.0 | 1.95 | 0.5 | 3.9 | 1.95 | 1.95 | 0.5 | 0.004 | |
| 14 | 0.25 | 1.0 | 1.95 | 15.6 | 31.3 | 0.5 | 0.5 | 0.5 | 15.6 | 1.95 | 1.95 | 1.0 | 0.004 | |
| 11 | 0.25 | 1.0 | 1.95 | 7.8 | 15.6 | 1.0 | 1.95 | 1.0 | 3.9 | 1.0 | 1.0 | 0.5 | 0.004 | |
| 12 | 0.25 | 1.0 | 1.0 | 3.9 | 7.8 | 1.0 | 0.5 | 0.5 | 7.8 | 1.0 | 1.0 | 1.0 | 0.005 | |
| 9D | 0.5 | 1.95 | 3.9 | 3.9 | 3.9 | 1.0 | 1.95 | 0.5 | 1.95 | 1.0 | 1.0 | 1.0 | 0.004 | |
| 45 | 0.5 | 1.95 | 1.0 | 1.95 | 1.95 | 1.95 | 1.95 | 1.0 | 7.8 | 1.0 | 3.9 | 1.0 | 0.005 | |
| 43 | 0.5 | 1.95 | 1.0 | 7.8 | 31.3 | 1.0 | 1.0 | 1.0 | 7.8 | 1.95 | 1.95 | 1.0 | 0.005 | |
| 46 | 1.0 | 7.8 | 7.8 | 3.9 | 3.9 | 3.9 | 3.9 | 1.95 | 15.6 | 7.8 | 7.8 | 1.95 | 0.005 | |
| 44A | 1.0 | 1.0 | 1.95 | 15.6 | 3.9 | 1.0 | 1.0 | 0.5 | 3.9 | 1.0 | 1.95 | 1.0 | 0.003 | |
| 47 | 0.5 | 1.0 | 3.9 | 3.9 | 15.6 | 1.95 | 1.95 | 1.0 | 15.6 | 3.9 | 1.95 | 1.0 | 0.004 | |
| 48 | 1.0 | 1.95 | 3.9 | 7.8 | 15.6 | 1.95 | 1.95 | 1.0 | 3.9 | 1.95 | 1.95 | 1.0 | 0.01 | |
| 29C | 1.0 | 3.9 | 1.95 | 3.9 | 7.8 | 1.95 | 1.95 | 1.95 | 7.8 | 3.9 | 3.9 | 1.95 | 0.004 | |
| 50 | 1.95 | 1.95 | 3.9 | 3.9 | 3.9 | 3.9 | 1.95 | 1.95 | 7.8 | 3.9 | 3.9 | 1.95 | 0.004 | |
| 51 | 1.95 | 1.95 | 3.9 | 3.9 | 3.9 | 3.9 | 3.9 | 1.95 | 7.8 | 3.9 | 3.9 | 1.95 | 0.004 | |
| 52 | 1.95 | 3.9 | 3.9 | 3.9 | 3.9 | 7.8 | 3.9 | 1.95 | 15.6 | 7.8 | 7.8 | 1.95 | 0.01 | |
| 72 | 7.8 | 31.3 | >62.5 | 62.5 | >62.5 | 62.5 | >62.5 | 15.6 | >62.5 | 31.3 | 31.3 | 7.8 | 0.1 | |
| 73 | 7.8 | 62.5 | >62.5 | 62.5 | >62.5 | >62.5 | 62.5 | 15.6 | >62.5 | >62.5 | 31.3 | 7.8 | 0.1 | |
| 70 | 7.8 | 31.3 | >62.5 | >62.5 | >62.5 | >62.5 | 62.5 | 7.8 | 62.5 | 15.6 | 31.3 | 7.8 | 0.1 | |
| 71 | 3.9 | 62.5 | >62.5 | 62.5 | 62.5 | 62.5 | 62.5 | 7.8 | 62.5 | 62.5 | 62.5 | 7.8 | 0.1 | |
| 74 | 15.6 | >62.5 | >62.5 | >62.5 | >62.5 | >62.5 | >62.5 | 15.6 | >62.5 | >62.5 | >62.5 | 15.6 | 0.1 | |
| 75 | 31.3 | >62.5 | >62.5 | >62.5 | >62.5 | >62.5 | >62.5 | 15.6 | >62.5 | >62.5 | >62.5 | 15.6 | 1.0 | |
| 65 | 1.0 | 3.9 | 7.8 | 3.9 | 7.8 | 3.9 | 3.9 | 1.0 | 7.8 | 15.6 | 15.6 | 1.95 | 0.01 | |
| 66 | 1.0 | 1.95 | 3.9 | 7.8 | 7.8 | 7.8 | 3.9 | 1.95 | 15.6 | 7.8 | 15.6 | 1.95 | 0.01 | |
| 67 | 1.0 | 1.95 | 15.6 | 7.8 | 7.8 | 7.8 | 3.9 | 1.95 | 31.3 | 31.3 | 15.6 | 3.9 | 0.01 | |
| 68 | 1.95 | 7.8 | 31.3 | 7.8 | 15.6 | 15.6 | 15.6 | 3.9 | 15.6 | 15.6 | 15.6 | 3.9 | 0.01 | |
| 69 | 1.95 | 7.8 | 31.3 | 15.6 | 15.6 | 31.3 | 15.6 | 3.9 | 15.6 | 15.6 | 15.6 | 3.9 | 0.1 | |
| 49 | 0.5 | 1.0 | 1.95 | 3.9 | 15.6 | 1.95 | 1.95 | 1.0 | 7.8 | 1.95 | 1.95 | 1.0 | 0.004 | |
| 64B | 1.0 | 1.95 | 3.9 | 1.95 | 7.8 | 1.95 | 7.8 | 1.0 | 7.8 | 1.95 | 3.9 | 1.0 | 0.01 | |
| 41C | 0.5 | 1.0 | 1.95 | 3.9 | 3.9 | 1.0 | 1.0 | 0.5 | 3.9 | 1.0 | 1.0 | 1.0 | 0.1 | |
| 30 | 1.95 | >62.5 | >62.5 | >250 | >62.5 | >62.5 | >62.5 | 3.9 | 31.3 | 15.6 | 7.8 | 1.0 | | 1.0 |
| 10C | 1.0 | 1.0 | 1.95 | 1.95 | 3.9 | — | — | 0.5 | 1.95 | 1.0 | — | 1.0 | 0.005 | |
| 83B | 15.6 | 31.3 | >125 | >125 | >62.5 | 15.6 | 15.6 | 7.8 | 31.3 | 31.3 | 31.3 | 31.3 | | 1.0 |
| 84 | 1.95 | 15.6 | >62.5 | >125 | >62.5 | 7.8 | 7.8 | 7.8 | 15.6 | 15.6 | 7.8 | 15.6 | | 1.0 |
| I | 31.3 | 125 | >500 | >500 | >500 | 125 | 250 | 31.3 | 125 | 125 | 125 | 125 | | 1.0 |
| II | 7.8 | 62.5 | 250 | >500 | 500 | 31.3 | 62.5 | 7.8 | 125 | 250 | 62.5 | 15.6 | | 1.0 |
| III | 125 | 250 | >500 | >500 | >500 | — | — | 62.5 | 500 | >500 | — | 500 | | 1.0 |
| IV | 125 | 250 | >500 | >500 | >500 | — | — | 62.5 | 500 | >500 | — | >500 | | 1.0 |
| V | 1.95 | 62.5 | >62.5 | >125 | >62.5 | — | — | 1.0 | 31.3 | 31.3 | — | 3.9 | | 1.0 |
| VI | 15.6 | 250 | 500 | >500 | >500 | — | — | 15.6 | 250 | 31.3 | — | 15.6 | | 1.0 |
| VII | 31.3 | 250 | 500 | >500 | >500 | — | — | 7.8 | 250 | 31.3 | — | 15.6 | | 1.0 |
| VIII | 31.3 | >250 | 500 | >500 | >500 | — | — | 7.8 | 125 | 125 | — | 15.6 | | 1.0 |
| IX | 3.9 | 31.3 | 250 | >500 | >500 | — | — | 3.9 | 31.3 | 31.3 | — | 7.8 | | 1.0 |

TABLE B

Effect of Serum on Bacteriostatic Activity
MIC (mcg/ml) vs. Indicated Bacteria

| Cpd. of Ex. No. | S. Aureus ATCC 6538 | | | E. Coli ATCC 8739 | | |
|---|---|---|---|---|---|---|
| | 0% Serum | 40% Serum | Fold Increase | 0% Serum | 40% Serum | Fold Increase |
| 79B | 0.25 | 7.8 | 32 | 0.5 | 15.6 | 32 |
| 22 | 0.25 | 3.9 | 16 | 0.5 | 3.9 | 8 |
| 33 | 0.125 | 1.95 | 16 | 0.25 | 3.9 | 16 |
| 26 | 0.125 | 1.95 | 16 | 0.5 | 7.8 | 16 |
| 24 | 0.125 | 1.95 | 16 | 0.25 | 7.8 | 32 |
| 58 | 0.25 | 3.9 | 16 | 0.5 | 15.6 | 32 |
| 3 | 0.39 | 3.12 | 8 | 0.78 | 25.0 | 32 |
| 1D | 0.195 | 3.12 | 16 | 1.56 | 25.0 | 16 |
| 7 | 0.10 | 1.56 | 16 | 0.39 | 12.5 | 32 |
| 5C | 0.10 | 3.12 | 32 | 0.78 | 25.0 | 32 |
| 13 | 0.25 | 31.2 | 128 | 1.0 | 31.2 | 32 |
| 11 | 0.5 | 7.8 | 16 | 0.5 | 31.2 | 64 |
| 9D | 0.5 | 7.8 | 16 | 1.0 | 62.5 | 64 |
| 29C | 0.5 | 7.8 | 16 | 3.9 | 62.5 | 16 |
| 41C | 0.25 | 7.8 | 32 | 1.0 | 62.5 | 64 |

TABLE C

Staining Potential and Effect of Saliva on Dental Plaque Preventive Activity

| Cpd. of Ex. No. | Dental Plaque Preventive Activity in 50% saliva Minimum Effective Conc. (%) | Staining Concentration (%) |
|---|---|---|
| 27 | | 0.05 |
| 24 | Ca. 0.005 | 0.05 |
| 25 | | 0.05 |
| 58 | Ca. 0.005 | 0.05 |
| 59 | | 0.05 |
| 56 | 0.1 | 0.05 |
| 3 | 0.1 | 0.05 |
| 4 | Ca. 0.005 | 0.005 |
| 5C | 0.05[1] | 0.005 |
| 6 | | 0.005 |
| 13 | | 0.005 |
| 14 | 0.1 | 0.05 |
| 11 | 0.05 | 0.05 |
| 12 | | 0.05 |
| 9D | Ca. 0.005 | 0.05 |
| 10 A, B | 0.005 | 0.05 |
| 44A | 0.005 | 0.05 |
| 47 | | 0.004 |
| 29C | | 0.004 |
| 50 | | 0.004 |
| 51 | | 0.004 |
| 49 | | 0.005 |

[1] No bacterial growth at this concentration, plaque formed at 0.005%

Table D

Acute Oral Toxicity (ALD$_{50}$)

| Cpd. of Ex. No. | Solution or Suspension | Dose, mg/kg, of Total Material | Mortality 24 Hrs | 7 Days |
|---|---|---|---|---|
| 23 | Aqueous Solution | 125 | 0/3 | 0/3 |
| | | 250 | 0/3 | 0/3 |
| | | 500 | ⅓ | ⅓ |
| | | 1000 | 3/3 | 3/3 |
| | | 7-Day ALD$_{50}$ = 625 mg/kg | | |
| 26 | Suspension in 1% G.T.[1] | 125 | 0/3 | 0/3 |
| | | 250 | 0/3 | 0/3 |
| | | 500 | 0/3 | 0/3 |
| | | 1000 | 0/3 | 0/3 |
| | | 7-Day ALD$_{50}$ = >1000 mg/kg | | |
| 27 | Aqueous Solution | 125 | 0/3 | ⅓ |
| | | 250 | 0/3 | 0/3 |
| | | 500 | ⅓ | ⅓ |
| | | 1000 | ⅓ | 3/3 |
| | | 7-Day ALD$_{50}$ = 250 mg/kg | | |
| 24 | Suspension in 1% G.T. | 125 | 0/3 | 0/3 |
| | | 250 | 0/3 | 0/3 |
| | | 500 | 0/3 | ⅓ |
| | | 1000 | 0/3 | 0/3 |
| 25 | Aqueous Solution | 7-Day ALD$_{50}$ = >1000 mg/kg | | |
| | | 250 | ⅓ | ⅓ |
| | | 500 | ⅓ | ⅓ |
| | | 1000 | 3/3 | 3/3 |
| | | 7-Day ALD$_{50}$ = 500 mg/kg | | |
| 3 | Suspension in 1% G.T. | 125 | 0/3 | 0/3 |
| | | 250 | 0/3 | 0/3 |
| | | 500 | 0/3 | ⅓ |
| | | 1000 | ⅓ | ⅓ |
| | | 7-Day ALD$_{50}$ = 1000 mg/kg | | |
| 4 | Suspension in 1% G.T. | 125 | 0/3 | 0/3 |
| | | 1250 | 0/3 | 0/3 |
| | | 500 | 0/3 | 0/3 |
| | | 1000 | 0/3 | 0/3 |
| | | 7-Day ALD$_{50}$ = >1000 mg/kg | | |
| 2 | Suspension in 1% G.T. | 125 | 0/3 | 0/3 |
| | | 250 | 0/3 | ⅓ |
| | | 500 | 0/3 | ⅓ |
| | | 1000 | 0/3 | ⅓ |
| | | 7-Day ALD$_{50}$ = 1000 mg/kg | | |
| 3 | Aqueous Solution | 125 | 0/3 | 0/3 |
| | | 250 | ⅓ | ⅓ |
| | | 500 | ⅔ | 3/3 |
| | | 1000 | 3/3 | 3/3 |
| | | 7-Day ALD$_{50}$ = 315 mg/kg | | |
| 5C | Suspension in 1% G.T. | 125 | 0/3 | 0/3 |
| | | 250 | 0/3 | 0/3 |
| | | 500 | 0/3 | 0/3 |
| | | 1000 | ⅓ | ⅓ |
| | | 7-Day ALD$_{50}$ = >1000 mg/kg | | |
| 6 | Aqueous Solution | 125 | ⅓ | ⅓ |
| | | 250 | 0/3 | ⅓ |
| | | 500 | ⅔ | ⅔ |
| | | 1000 | 3/3 | 3/3 |
| | | 7-Day ALD$_{50}$ = 315 mg/kg | | |
| 1D | Suspension in 1% G.T. | 125 | 0/3 | 0/3 |
| | | 250 | 0/3 | 0/3 |
| | | 500 | ⅓ | ⅓ |
| | | 1000 | ⅔ | ⅔ |
| | | 7-Day ALD$_{50}$ = 750 mg/kg | | |
| 11 | Suspension in 1% G.T. | 125 | 0/3 | 0/3 |
| | | 250 | 0/3 | 0/3 |
| | | 500 | 0/3 | ⅓ |
| | | 1000 | 0/3 | 0/3 |
| | | 7-Day ALD$_{50}$ = >1000 mg/kg | | |
| 12 | Aqueous Solution | 125 | 0/3 | 0/3 |
| | | 250 | 0/3 | 0/3 |
| | | 500 | ⅓ | ⅓ |
| | | 1000 | ⅔ | ⅔ |
| | | 7-Day ALD$_{50}$ = 750 mg/kg | | |
| 9D | Suspension in 1% G.T. | 25 | 0/3 | 0/3 |
| | | 250 | 0/3 | 0/3 |
| | | 500 | 0/3 | 0/3 |
| | | 1000 | 0/3 | 0/3 |
| | | 7-Day ALD$_{50}$ = >1000 mg/kg | | |
| 10A,B | Aqueous Solution | 125 | 0/3 | 0/3 |
| | | 250 | 0/3 | 0/3 |
| | | 500 | 0/3 | 0/3 |
| | | 1000 | 0/3 | 0/3 |
| | | 7-Day ALD$_{50}$ = >1000 mg/kg | | |
| 58 | Suspension in 1% G.T. | 125 | 0/3 | 0/3 |
| | | 250 | 0/3 | 0/3 |
| | | 500 | 0/3 | 0/3 |
| | | 1000 | 0/3 | 0/3 |
| | | 7-Day ALD$_{50}$ = >1000 mg/kg | | |
| 59 | Aqueous Solution | 125 | 0/3 | 0/3 |
| | | 250 | 0/3 | 0/3 |
| | | 500 | ⅓ | ⅔ |
| | | 1000 | ⅓ | ⅓ |
| | | 7-Day ALD$_{50}$ = 750 mg/kg | | |
| 56 | Suspension in 1% G.T. | 125 | 0/3 | 0/3 |
| | | 250 | 0/3 | 0/3 |
| | | 500 | 0/3 | 0/3 |
| | | 1000 | ⅓ | ⅓ |
| | | 7-Day ALD$_{50}$ = >1000 mg/kg | | |
| 14 | Suspension in 1% G.T. | 125 | 0/3 | 0/3 |
| | | 250 | 0/3 | 0/3 |
| | | 500 | 0/3 | 0/3 |

Table D-continued

Acute Oral Toxicity (ALD$_{50}$)

| Cpd. of Ex. No. | Solution or Suspension | Dose, mg/kg, of Total Material | Mortality 24 Hrs | 7 Days |
|---|---|---|---|---|
| | | 1000 | 0/3 | |
| | 7-Day ALD$_{50}$ = >1000 mg/kg | | | |
| 44A | Suspension in 1% G.T. | 125 | 0/3 | 0/3 |
| | | 250 | 0/3 | 0/3 |
| | | 500 | 0/3 | 0/3 |
| | | 1000 | 0/3 | 0/3 |
| | 7-Day ALD$_{50}$ = >1000 mg/kg | | | |
| 29C | Suspension in 1% G.T. | 125 | 0/3 | 0/3 |
| | | 250 | 0/3 | 0/3 |
| | | 500 | 0/3 | 0/3 |
| | | 1000 | 0/3 | 0/3 |
| | 7-Day ALD$_{50}$ = >1000 mg/kg | | | |
| 41C | Suspension in 1% G.T. | 125 | 0/3 | 0/3 |
| | | 250 | 0/3 | 0/3 |
| | | 500 | 0/3 | 0/3 |
| | | 1000 | 0/3 | 0/3 |
| | 7-Day ALD$_{50}$ = >1000 mg/kg | | | |

[1]G.T. = Gum Tragacanth

I claim:

1. A compound having the formula

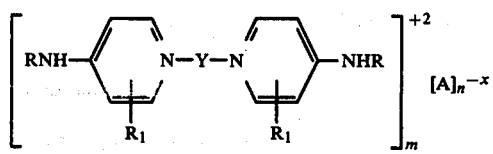

wherein:
Y is an alkylene group containing from 4 to 18 carbon atoms and separating the two 4-(R—NH)-1-pyridinyl groups by from 4 to 18 carbon atoms;
R is an alkyl group containing from 6 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl;
$R_1$ is hydrogen or lower alkyl;
A is an anion;
m is 1 or 3;
n is 1 or 2;
x is 1, 2 or 3; and
wherein
(m)(2)=(n)(x).

2. A compound having the formula

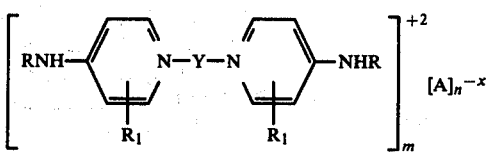

wherein:
Y is an alkylene group containing from 4 to 18 carbon atoms and separating the two 4—(R—NH)-1-pyridinyl groups by from 4 to 18 carbon atoms;
R is an alkyl group containing from 6 to 18 carbon atoms;
$R_1$ is hydrogen or lower alkyl;
A is an anion;
m is 1 or 3;
n is 1 or 2;
x is 1, 2 or 3; and
wherein
(m)(2)=(n)(x).

3. A compound according to claim 2 wherein $R_1$ is hydrogen, Y is $(CH_2)_w$ and w is from 4 to 18.

4. A compound according to claim 3 wherein w is from 8 to 12.

5. A compound according to claim 4 wherein R is an alkyl group containing from 7 to 9 carbon atoms.

6. A compound according to claim 5 wherein A is chloride or bromide.

7. A compound having the formula

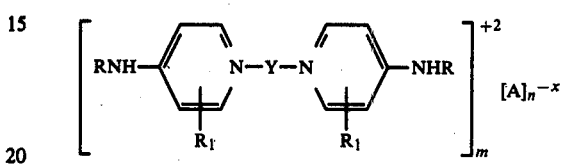

wherein:
Y is an alkylene group containing from 4 to 18 carbon atoms and separating the two 4—(R—NH)-1-pyridinyl groups by from 4 to 18 carbon atoms;
R is a cycloalkyl group containing from 5 to 7 carbon atoms;
$R_1$ is hydrogen or lower alkyl;
A is an anion;
m is 1 or 3;
n is 1 or 2;
x is 1, 2 or 3; and
wherein
(m)(2)=(n)(x).

8. A compound according to claim 7 wherein $R_1$ is hydrogen, Y is $(CH_2)_w$ and w is from 4 to 18.

9. A compound according to claim 8 wherein w is from 8 to 12 and R is cyclohexyl.

10. A compound having the formula

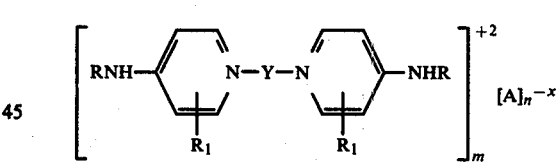

wherein:
Y is an alkylene group containing from 4 to 18 carbon atoms and separating the two 4-(R-NH)-1-pyridinyl groups by from 4 to 18 carbon atoms;
R is phenyl substituted by methylenedioxy or one or two substituents selected from the group consisting of halogen, lower-alkyl, lower-alkoxy, nitro, cyano and trifluoromethyl;
$R_1$ is hydrogen or lower alkyl;
A is an anion;
m is 1 or 3;
n is 1 or 2;
x is 1, 2 or 3; and
wherein
(m)(2)=(n)(x).

11. A compound according to claim 10 wherein $R_1$ is hydrogen, Y is $(CH_2)_w$ and w is from 4 to 18.

12. A compound according to claim 11 wherein w is from 8 to 12 and R is p-chlorophenyl.

13. A compound having the formula

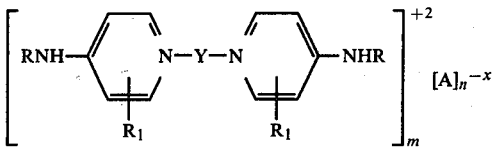

wherein:
Y is an alkylene group containing from 4 to 18 carbon atoms and separating the two 4-(R-NH)-1-pyridinyl groups by from 4 to 18 carbon atoms;
R is benzyl;
$R_1$ is hydrogen or lower alkyl;
A is an anion;
m is 1 or 3;
n is 1 or 2;
x is 1, 2 or 3; and
wherein
(m)(2)=(n)(x).

14. A compound according to claim 13 wherein $R_1$ is hydrogen, Y is $(CH_2)_w$ and w is from 8 to 12.

15. 1,12-Bis-[4-(heptylamino)-1-pyridinium]dodecane dibromide according to claim 6.

16. 1,12-Bis-[4-(heptylamino)-1-pyridinium]dodecane dichloride according to claim 6.

17. 1,10-Bis-[4-(octylamino)-1-pyridinium]decane dibromide according to claim 6.

18. 1,10-Bis-[4-(octylamino)-1-pyridinium]decane dichloride according to claim 6.

19. 1,12-Bis-[4-(2-ethylhexylamino)-1-pyridinium]dodecane dibromide according to claim 6.

20. 1,12-Bis-[4-(2-ethylhexylamino)-1-pyridinium]dodecane dichloride according to claim 6.

21. A compound selected from the group consisting of:
1,9-bis-[4-(heptylamino)-1-pyridinium]nonane dibromide,
1,10-bis-[4-(2-ethylhexylamino)-1-pyridinium]-decane dibromide,
1,10-bis-[4-(octylamino)-1-pyridinium]decane dichloride,
1,9-bis-[4-(octylamino)-1-pyridinium]nonane dibromide,
1,12-bis-[4-(heptylamino)-1-pyridinium]dodecane dichloride,
1,8-bis-[4-(octylamino)-1-pyridinium]octane dibromide and
1,10-bis-[4-(octylamino)-1-pyridinium]decane dibromide.

22. 1.9-Bis-[4-(heptylamino)-1-pyridinium]nonane dibromide according to claim 21.

23. 1,10-Bis-[4-(2-ethylhexylamino)-1-pyridinium]-decane dibromide according to claim 21.

24. 1,10-Bis-[4-(propylamino)-1-pyridinium]decane dibromide.

25. An antimicrobial composition suitable for topical administration comprising an effective amount of a compound according to claim 1 wherein A is a pharmaceutically acceptable anion and a compatible, pharmaceutically acceptable carrier.

26. A skin-cleansing composition comprising an antimicrobially effective amount of a compound according to claim 1 wherein A is a pharmaceutically acceptable anion, a compatible, pharmaceutically acceptable surfactant and a compatible, pharmaceutically acceptable carrier.

27. A skin-cleansing composition comprising an antimicrobially effective amount of a compound according to claim 5 wherein A is a pharmaceutically acceptable anion, a compatible pharmaceutically acceptable surfactant and a compatible, pharmaceutically acceptable carrier.

28. An oral hygiene composition for the prevention of dental plaque comprising an effective amount of a compound according to claim 21 wherein A is a pharmaceutically acceptable anion and a compatible, pharmaceutically acceptable carrier.

29. An antimicrobial composition suitable for application to inanimate surfaces comprising an effective amount of a compound according to claim 1 in admixture with a compatible vehicle.

30. A method for controlling microorganisms which comprises contacting said microorganisms with an antimicrobially effective amount of a compound of the formula

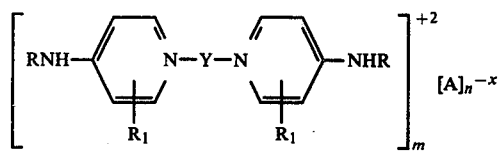

wherein:
Y is an alkylene group containing from 4 to 18 carbon atoms and separating the two 4-(R-NH)-1-pyridinyl groups by from 4 to 18 carbon atoms;
R is hydrogen, an alkyl group containing from 1 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl;
$R_1$ is hydrogen or lower alkyl;
A is an anion;
m is 1 or 3;
n is 1 or 2;
x is 1, 2 or 3; and
wherein
(m)(2)=(n)(x).

31. A method according to claim 30 wherein R is hydrogen.

32. A method according to claim 30 wherein R is an alkyl group containing from 1 to 18 carbon atoms, a cycloalkyl group containing from 5 to 7 carbon atoms, benzyl, or phenyl substituted by methylenedioxy or one or two substituents selected from the group consisting of halogen, lower-alkyl, lower-alkoxy, nitro, cyano and trifluoromethyl.

33. A method for controlling microorganisms which comprises contacting said microorganisms with an antimicrobially effective amount of a compound according to claim 3.

34. A method for controlling microorganisms which comprises contacting said microorganisms with an antimicrobially effective amount of a compound according to claim 5.

35. A method according to claim 34 wherein the antimicrobially effective agent is 1,12-bis-[4-(heptylamino)-1-pyridinium]dodecane dibromide.

36. A method according to claim 34 wherein the antimicrobially effective agent is 1,12-bis-[4-(heptylamino)-1-pyridinium]dodecane dichloride.

37. A method according to claim 34 wherein the antimicrobially effective agent is 1,10-bis-[4-(octylamino)-1-pyridinium]decane dibromide.

38. A method according to claim 34 wherein the antimicrobially effective agent is 1,10-bis-[4-(octylamino)-1-pyridinium]decane dichloride.

39. A method according to claim 34 wherein the antimicrobially effective agent is 1,12-bis-[4-(2-ethylhexylamino)-1-pyridinium]dodecane dibromide.

40. A method according to claim 34 wherein the antimicrobially effective agent is 1,12-bis-[4-(2-ethylhexylamino)-1pyridinium]dodecane dichloride.

41. A method of treating teeth for preventing the formation of dental plaque thereon which comprises contacting the teeth with an effective amount of a compound according to claim 21.

42. A method according to claim 41 wherein the dental plaque-preventive agent is 1,9-bis-[4-(heptylamino)-1-pyridinium]nonane dibromide.

43. A method according to claim 41 wherein the dental plaque-preventive agent is 1,10-bis-[4-(2-ethylhexylamino)-1-pyridinium]decane dibromide.

44. A method according to claim 41 wherein the dental plaque-preventive agent is 1,10-bis-[4-(octylamino)-1-pyridinium]decane dichloride.

45. A method according to claim 41 wherein the dental plaque-preventive agent is 1,9-bis-[4-(octylamino)-1-pyridinium]nonane dibromide.

* * * * *